(12) United States Patent
Kelly et al.

(10) Patent No.: US 12,121,293 B2
(45) Date of Patent: *Oct. 22, 2024

(54) NEUROMODULATION CATHETERS AND ASSOCIATED SYSTEMS AND METHODS

(71) Applicant: Medtronic Ireland Manufacturing Unlimited Company, Dublin (IE)

(72) Inventors: Brian Kelly, Oranmore (IE); Micheál Moriarty, Galway (IE)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/933,691

(22) Filed: Sep. 20, 2022

(65) Prior Publication Data

US 2023/0010636 A1 Jan. 12, 2023

Related U.S. Application Data

(63) Continuation of application No. 16/983,408, filed on Aug. 3, 2020, now Pat. No. 11,464,563, which is a continuation of application No. 14/691,389, filed on Apr. 20, 2015, now Pat. No. 10,736,690.

(60) Provisional application No. 61/983,812, filed on Apr. 24, 2014.

(51) Int. Cl.
*A61B 18/14* (2006.01)
*A61B 18/00* (2006.01)

(52) U.S. Cl.
CPC ............ *A61B 18/1492* (2013.01); *A61B 2018/00178* (2013.01); *A61B 2018/00404* (2013.01); *A61B 2018/00434* (2013.01); *A61B 2018/00511* (2013.01); *A61B 2018/00577* (2013.01);

(Continued)

(58) Field of Classification Search
CPC .......... A61B 18/1492; A61B 2017/003; A61B 2018/00404; A61B 2018/00434; A61B 2018/00511; A61B 2018/00577; A61B 2018/00821; A61B 2018/00916; A61B 2018/1435; A61B 2018/1467
See application file for complete search history.

(56) References Cited

U.S. PATENT DOCUMENTS 5,560,358 A 10/1996 Arnold et al.
6,746,446 B1* 6/2004 Hill, III ............ A61B 18/1492
604/95.04
2009/0247018 A1 10/2009 Kast et al.
(Continued)

FOREIGN PATENT DOCUMENTS

EP 1654980 A1 5/2006

OTHER PUBLICATIONS

Extended Search Report from counterpart European Application No. 24168286.3 dated Jul. 12, 2024, 7 pp.

*Primary Examiner* — Tigist S Demie
(74) *Attorney, Agent, or Firm* — Shumaker & Sieffert, P.A.

(57) ABSTRACT

Methods for treating a patient using therapeutic renal neuromodulation and associated devices, systems, and methods are disclosed herein. One aspect of the present technology, for example, is directed to a catheter apparatus including an elongated shaft defined by a braid embedded within a polymer. The braid can include one or more thermocouple assemblies intertwined with a braiding element. The thermocouple assemblies can be coupled to one or more electrodes at a distal portion of the shaft.

20 Claims, 21 Drawing Sheets

(52) U.S. Cl.
CPC ............... *A61B 2018/00821* (2013.01); *A61B 2018/1435* (2013.01); *A61B 2018/1467* (2013.01)

(56) References Cited

U.S. PATENT DOCUMENTS

2010/0273355 A1    10/2010   Gleason et al.
2012/0116383 A1*   5/2012    Mauch .............. A61M 25/0138
                                                      606/33

* cited by examiner

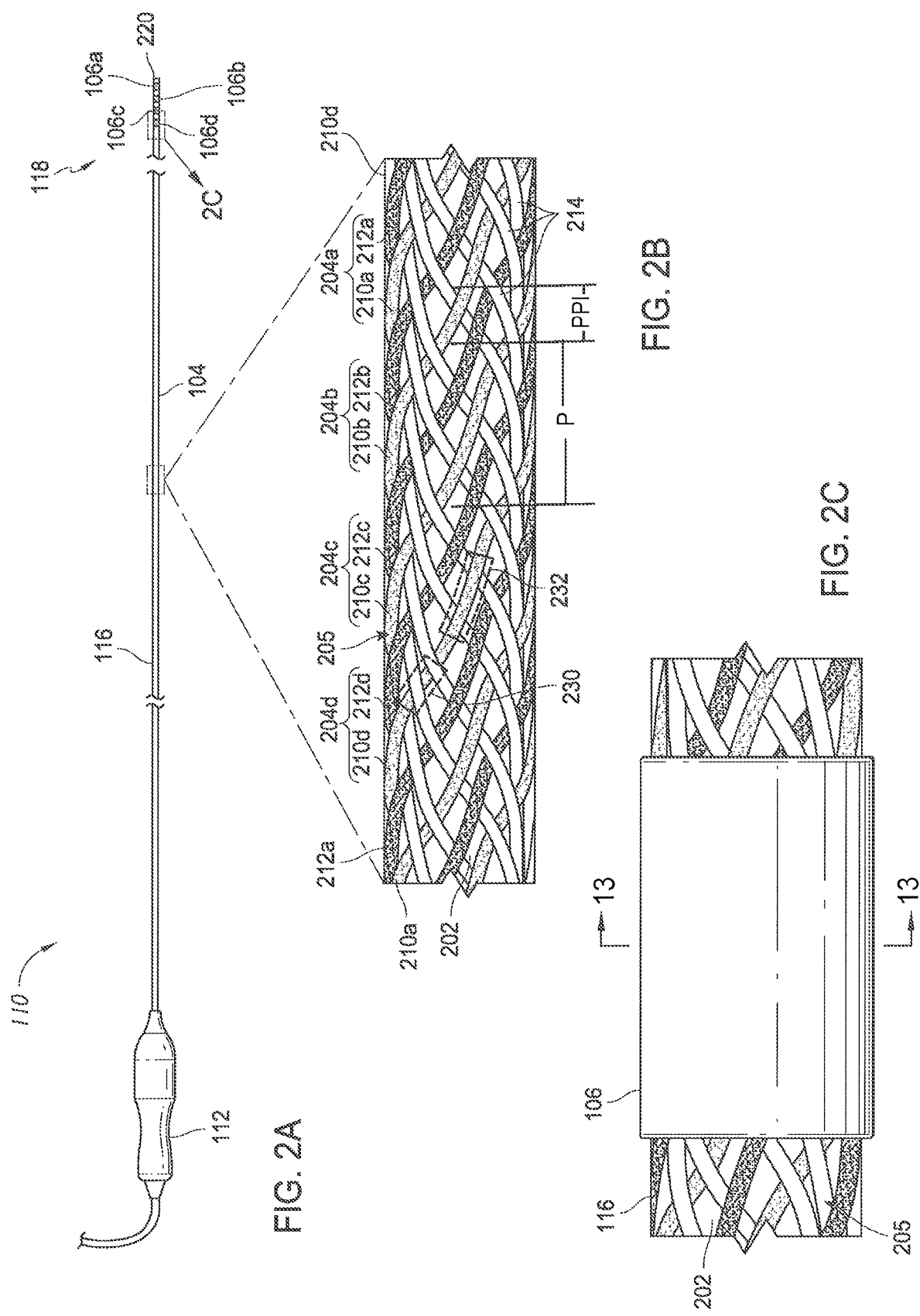

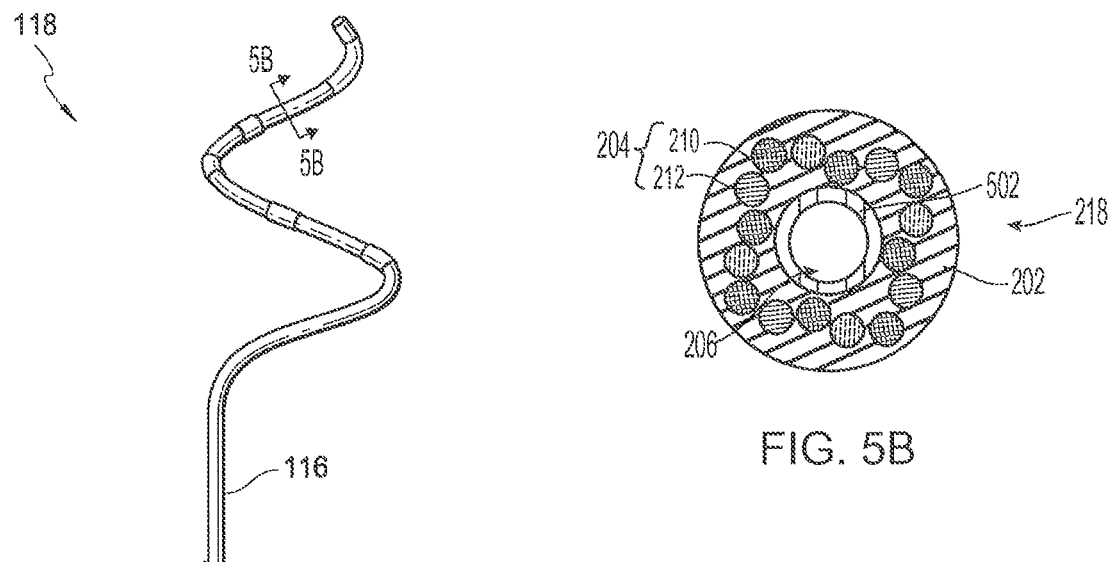
FIG. 5A
FIG. 5B
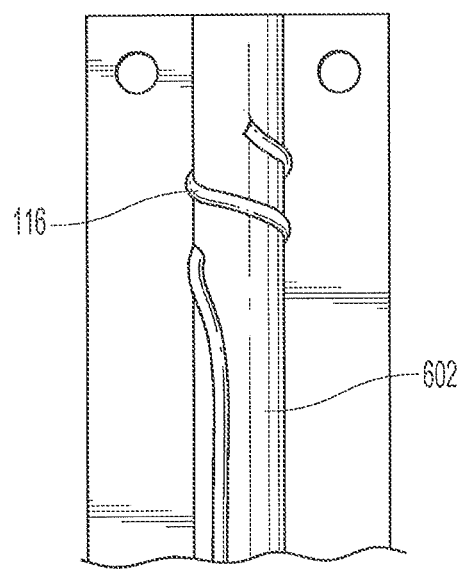
FIG 6

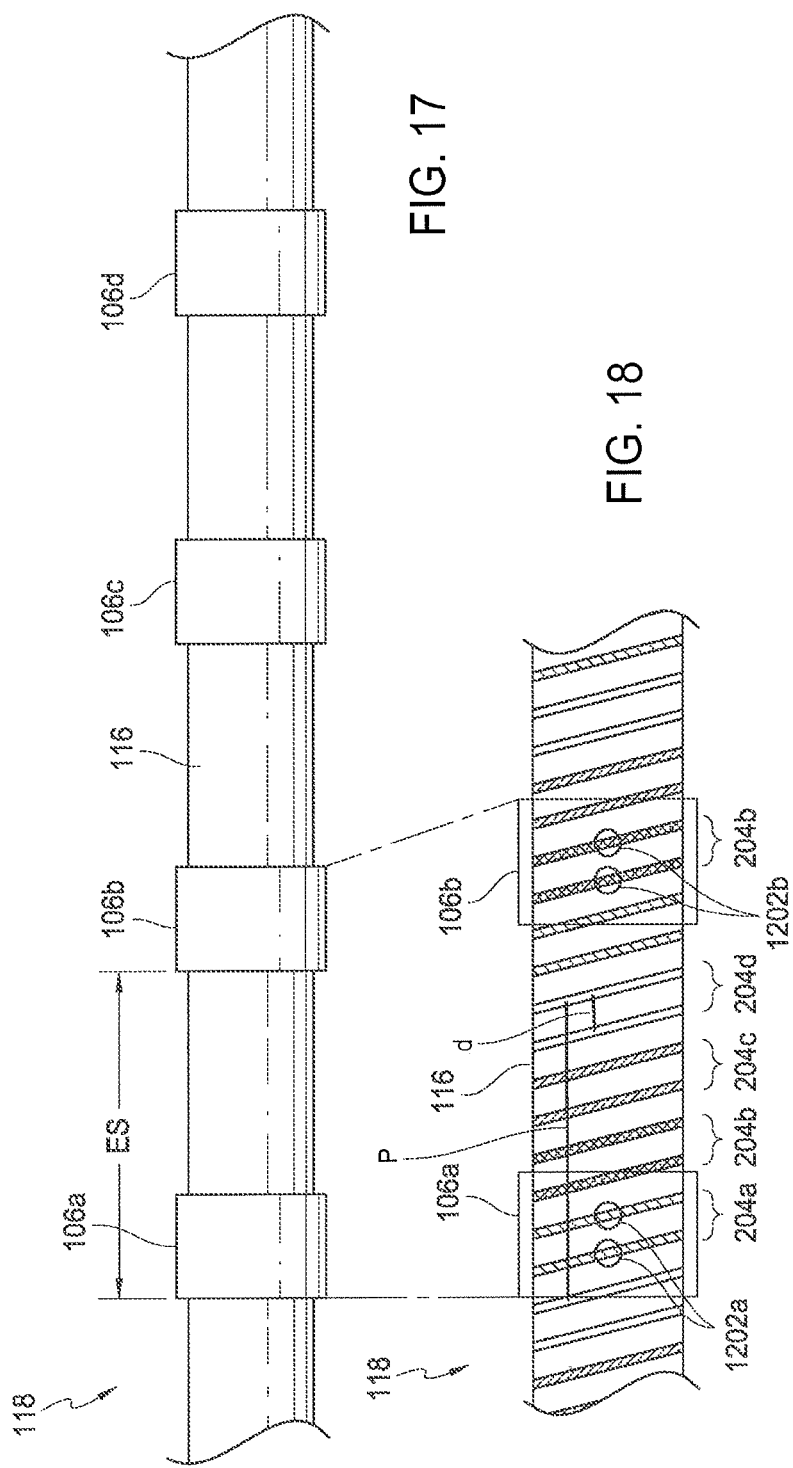

| Pattern | Steps |
|---|---|
| ABCDABCDABCDABCDABCDABCDABCDABCDABCDABCDABCDABCDABCD | (2) |
| ABCDABCDABCDABCDABCDABCDABCDABCDABCDABCDABCDABCDABCD | (10) |
| ABCDABCDABCDABCDABCDABCDABCDABCDABCDABCDABCDABCDABCD | (18) |
| ABCDABCDABCDABCDABCDABCDABCDABCDABCDABCDABCDABCDABCD | (26) |

FIG. 19

| Pattern | Steps |
|---|---|
| ABCDABCDABCDABCDABCDABCDABCDABCDABCDABCDABCDABCDABCD | (6) |
| ABCDABCDABCDABCDABCDABCDABCDABCDABCDABCDABCDABCDABCD | (14) |
| ABCDABCDABCDABCDABCDABCDABCDABCDABCDABCDABCDABCDABCD | (22) |
| ABCDABCDABCDABCDABCDABCDABCDABCDABCDABCDABCDABCDABCD | (30) |

FIG. 20

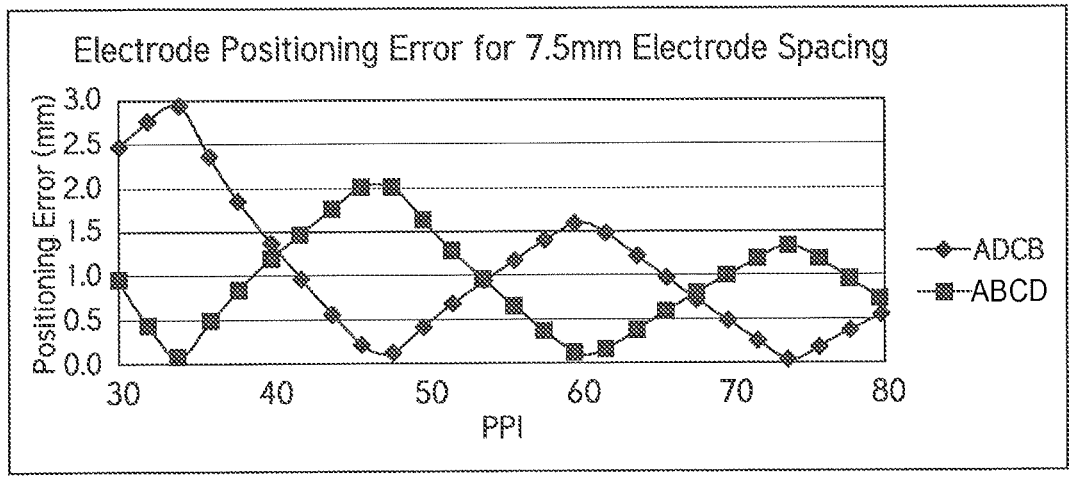

FIG. 21

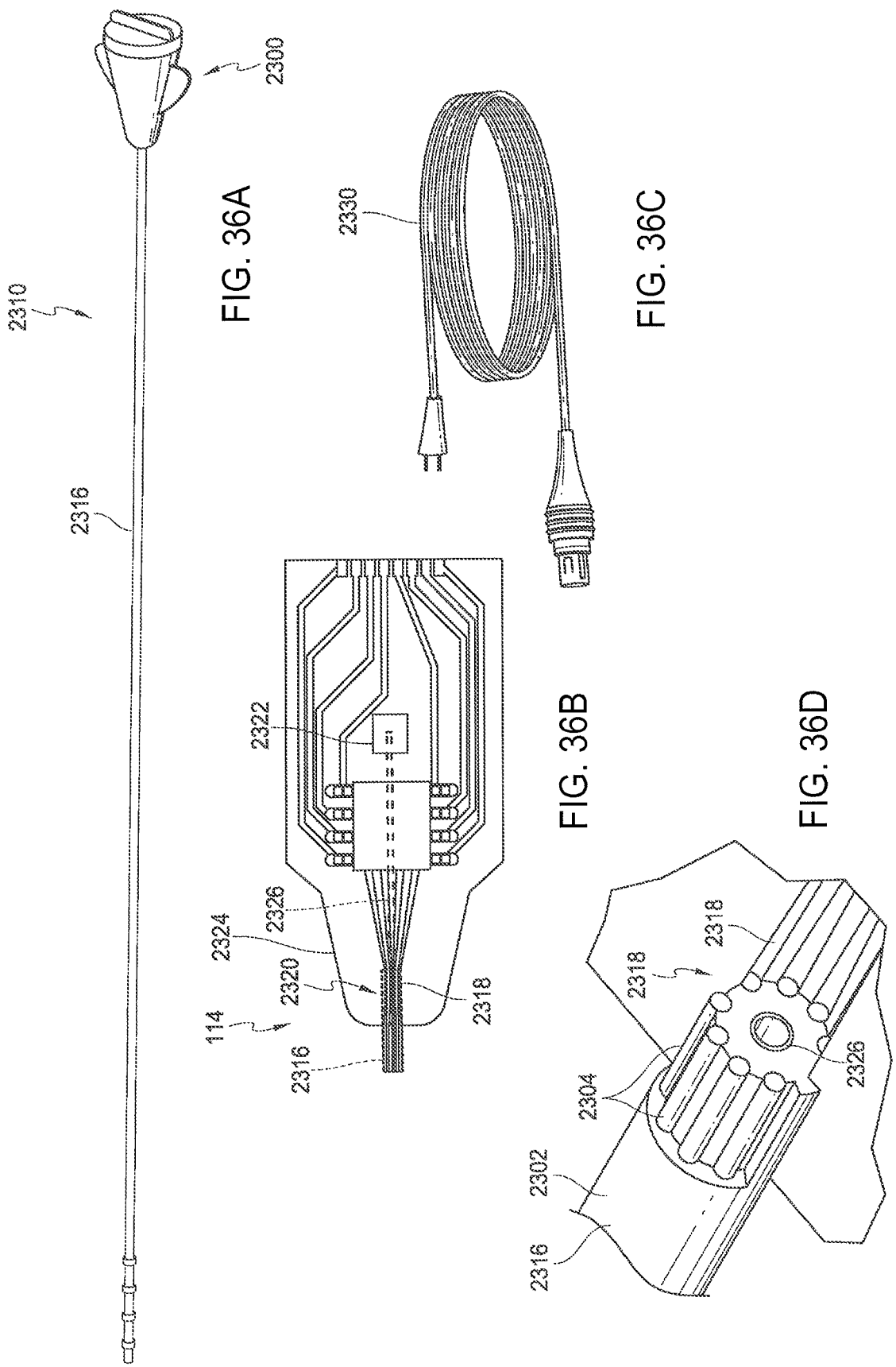

NEUROMODULATION CATHETERS AND ASSOCIATED SYSTEMS AND METHODS

CROSS-REFERENCE TO RELATED APPLICATIONS

This application is a continuation application of U.S. patent application Ser. No. 16/983,408, entitled "Neuromodulation Catheters and Associated Systems and Methods," filed on Aug. 3, 2020, which is a continuation application of U.S. patent application Ser. No. 14/691,389, entitled "Neuromodulation Catheters and Associated Systems and Methods," filed on Apr. 20, 2015 and issued as U.S. Pat. No 10,736,690, which claims the benefit of U.S. Provisional Patent Application No. 61/983,812, entitled, "Neuromodulation Catheters Having Braided Shafts and Associated Systems and Methods." filed on Apr. 24, 2014, the disclosures of each of which are incorporated herein by reference in their entirety.

TECHNICAL FIELD

The present technology relates generally to neuromodulation devices and methods of deployment. Some embodiments, for example, are directed to neuromodulation catheters (e.g., having braided shafts) and associated methods of use and manufacture.

BACKGROUND

The sympathetic nervous system (SNS) is a primarily involuntary bodily control system typically associated with stress responses. SNS fibers that innervate tissue are present in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiologies of hypertension, states of volume overload (such as heart failure), and progressive renal disease.

Sympathetic nerves innervating the kidneys terminate in the blood vessels, the juxtaglomerular apparatus, and the renal tubules. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone and likely contribute to increased blood pressure in hypertensive patients. For example, reduced renal blood flow and glomerular filtration rate as a result of renal sympathetic efferent stimulation is likely a cornerstone of the loss of renal function in cardiorenal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others.

Recently, neuromodulation devices have been developed that may reduce sympathetic nerve activity by applying an energy field to a target site in the renal blood vessel (e.g., via radio frequency ablation) and may thereby reduce blood pressure in patients with treatment-resistant hypertension. A number of neuromodulation devices utilize one or more thermocouples ("TC") to measure temperature at or near an electrode. The presence of TC wires within the catheter shaft, particularly in neuromodulation devices having two or more electrodes, can make the shaft bulky, stiff, and/or relatively expensive to manufacture.

BRIEF DESCRIPTION OF THE DRAWINGS

Many aspects of the present technology can be better understood with reference to the following drawings. Furthermore, components can be shown as transparent in certain views for clarity of illustration only and not to indicate that the illustrated component is necessarily transparent. The components in the drawings are not necessarily to scale. Instead, emphasis is placed on illustrating clearly the principles of the present technology.

FIG. 2A is a side view of the catheter shown in FIG. 1A in a low-profile configuration in accordance with the present technology.

FIGS. 2B and 2C are enlarged views of a portion of a shaft of the catheter shown in FIG. 2A.

FIG. 5A is a side view of a distal portion of the shaft in an expanded configuration, the shaft configured in accordance with an embodiment of the present technology.

FIG. 5B is a cross-sectional end view of the distal portion of the shaft taken along line 5B-5B in FIG. 5A.

FIG. 6 is a side view of the distal portion of the shaft on a mandrel during a stage of manufacturing in accordance with an embodiment of the present technology.

FIG. 17 is a side view of the distal portion of a shaft in a low-profile or delivery configuration showing an electrode spacing, the shaft configured in accordance with the present technology.

FIG. 18 is a schematic representation of an electrode placement pattern for a portion of the shaft shown in FIG. 17.

FIG. 19 is a table showing ABCD-patterned electrode spacing arrangements configured in accordance with an embodiment of the present technology.

FIG. 20 is a table showing ADCB-patterned electrode spacing arrangements configured in accordance with an embodiment of the present technology.

FIG. 21 is a graph showing picks per inch ("PPI") versus electrode positioning error for an electrode spacing of 7.5 mm.

FIG. 36A is a perspective view of a portion of a catheter configured in accordance with another embodiment of the present technology.

FIG. 36B is a perspective, enlarged view of a proximal portion of the catheter shown in FIG. 36A.

FIG. 36C is a perspective view of a connector for use with the catheter shown in FIG. 36A.

FIG. 36D is a perspective, enlarged view of a proximal portion of the catheter shown in FIG. 36A.

DETAILED DESCRIPTION

The present technology is directed to devices and methods for deployment and positioning of neuromodulation devices. Some embodiments of the present technology, for example, are directed to neuromodulation catheters having braided shafts and associated systems and methods. In certain embodiments, the neuromodulation catheters may have braided shafts. Specific details of several embodiments of the technology are described below with reference to FIGS. 1A-37B. Although many of the embodiments are described below with respect to systems, devices, and methods for renal neuromodulation, other applications (e.g., neuromodulation of other non-renal nerves, treatments other than neuromodulation, etc.) and other embodiments in addition to those described herein are within the scope of the technology. Additionally, several other embodiments of the technology can have different configurations, components, or procedures than those described herein. For example, although the present technology is illustrated and explained with respect to a four-electrode catheter, catheters having more or fewer than four electrodes are also within the scope of the technology (e.g., one, two, three, five, etc.). A person of ordinary skill in the art, therefore, will accordingly understand that the technology can have other embodiments with additional elements, or the technology can have other embodiments without several of the features shown and described below with reference to FIGS. 1A-37B.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. System Overview

Figure 1B:
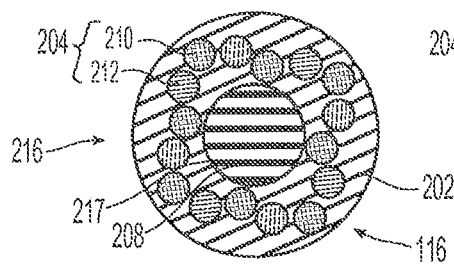
FIG. 1B is a cross-sectional end view of the catheter shaft in FIG. 1A taken along line 1B-1B.
Figure 1C:
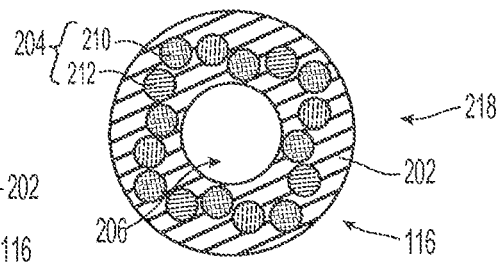
FIG. 1C is a cross-sectional end view of the catheter shaft in FIG. 1A taken along line 1C-1C.
Figure 1A:
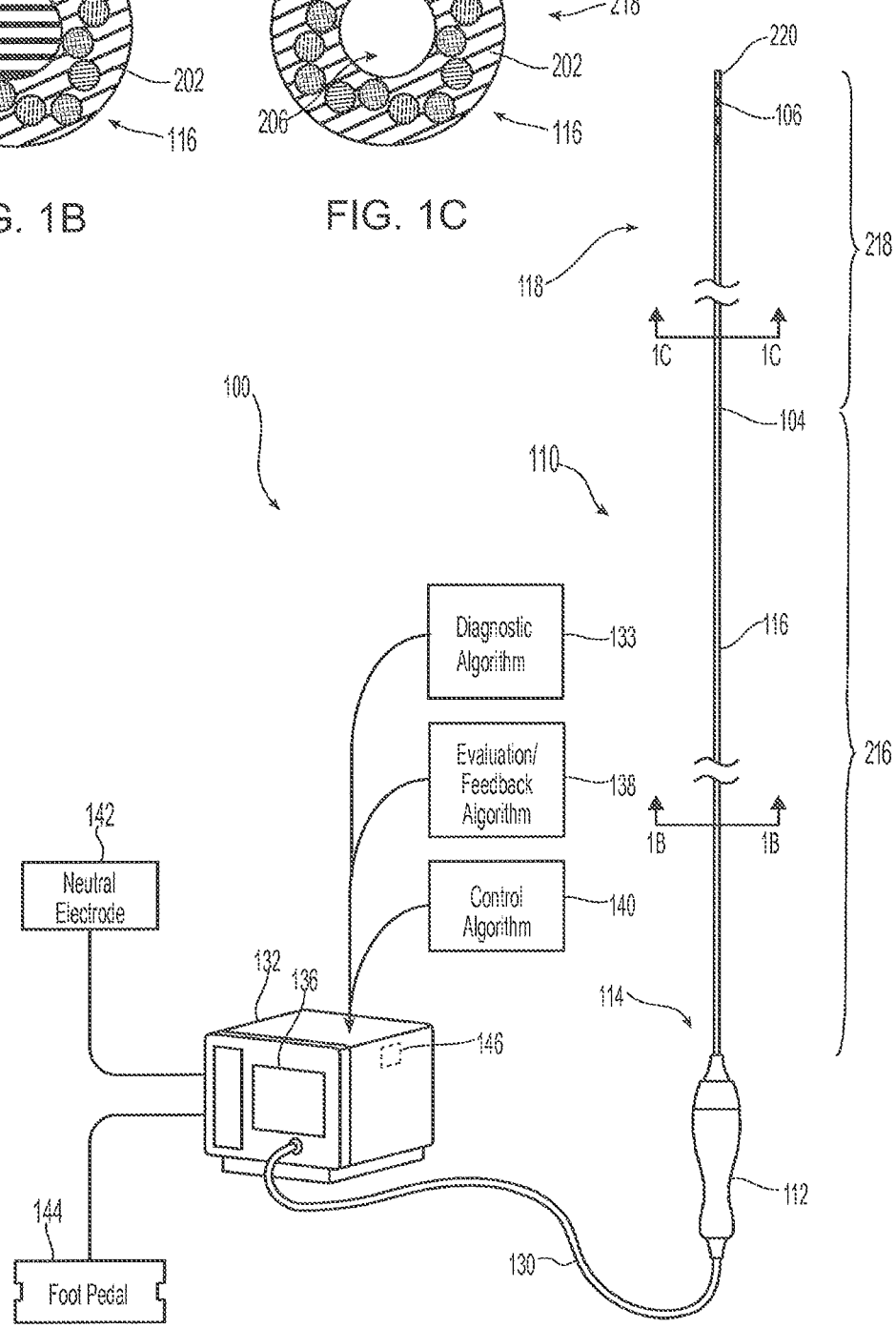
FIG. 1A is a partially schematic illustration of a neuromodulation system configured in accordance with an embodiment of the present technology.
Figure 3:
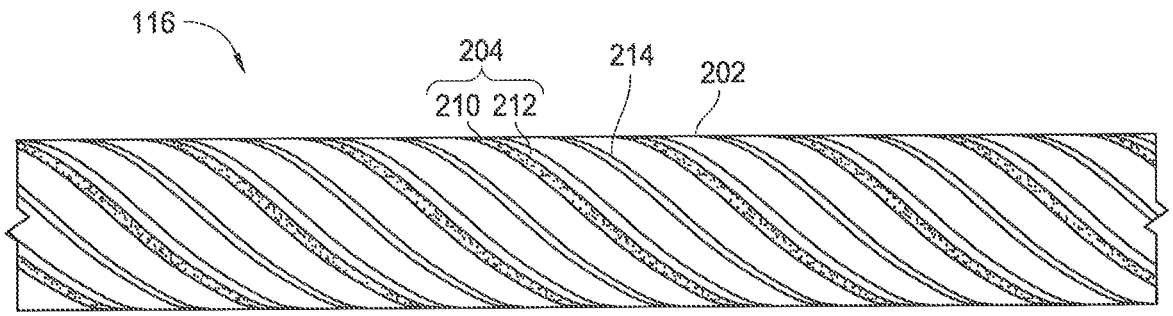
FIG. 3 is an enlarged side view of a portion of the shaft having TC assemblies and braiding element(s) wrapped in the same direction, the shaft configured in accordance with several embodiments of the present technology.
Figure 4:
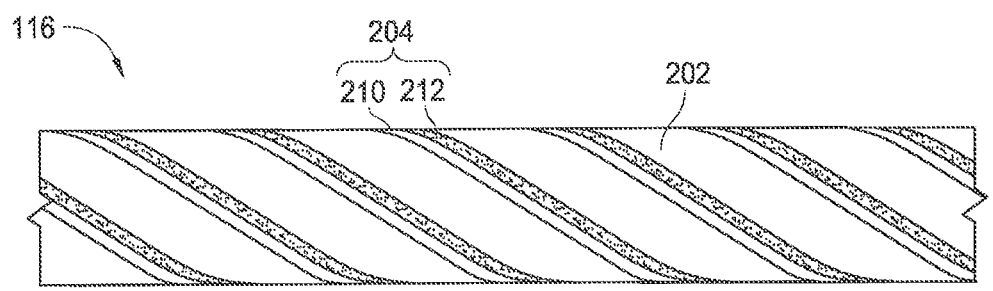
FIG. 4 is an enlarged side view of a portion of the shaft having a braid that only includes TC assemblies (and not braiding elements), the shaft configured in accordance with several embodiments of the present technology.

FIG. 1A is a partially-schematic perspective view of a neuromodulation system 100 ("system 100") configured in accordance with an embodiment of the present technology. The system 100 includes an intravascular catheter 110 operably coupled to an energy source or energy generator 132 via a connector 130 (e.g., a cable). The catheter 110 can include an elongated shaft 116 having a proximal portion 114 and a distal portion 118 carrying one or more electrodes 106. The catheter 110 also includes a handle assembly 112 at the proximal portion 114. The elongated shaft 116 is configured to intravascularly locate the distal portion 118 at a treatment location within a renal blood vessel or within another suitable body lumen (e.g., within a ureter) of a human patient. As shown in the cross-sectional end views of the shaft 116 in FIGS. 1B and 1C, the shaft 116 can be a flexible, tubular structure composed of a polymer jacket 202 and a plurality of TC assemblies 204 at least partially embedded within the polymer jacket 202. A distal portion of each of the TC assemblies 204 can be electrically coupled to a corresponding electrode 106. As such, the TC assemblies 204 may extend along the length of the shaft 116 and provide an electrical connection between the handle assembly 112 and the electrodes 106 at the distal portion 118 of the shaft 116. The structure and composition of the shaft 116 is discussed in greater detail below with reference to FIGS. 2A-37D.

The shaft 116 can further include a rapid-exchange ("RX") port 104 ("port 104") configured to receive a guidewire (not shown) therethrough. As shown in FIG. 1A, the shaft 116 can include a first section 216 extending from the handle 112 to the port 104, and a second section 218 extending distally from the port 104 to a distal end 220 of the shaft 116. As shown in FIG. 1B, the first section 216 can be substantially solid throughout its cross-section (e.g., no central lumen). For example, the first section 216 can include a generally cylindrical elongated member 208, such as a mandrel, that comprises a central portion of the first section 216. The TC assemblies 204 may be wrapped about the elongated member 208. The elongated member 208 can extend from the proximal portion 114 of the shaft 116 to the port 104. As shown in FIG. 1B, an outer circumference 217 of the elongated member 208 can abut an inner surface of the polymer jacket 202. Such a configuration may reduce the profile of the shaft 116, improve rotational force transmission along the shaft 116 when a rotational force is applied to the proximal portion 114 of the shaft (e.g., by the handle 112), and/or improve axial strength of the shaft 116. In some embodiments, the first section 216 can include an elongated member having other shapes and configurations and/or can be filled with one or more materials (e.g., a polymer filling). In certain embodiments, such as those including a catheter 110 configured to receive a guidewire via an over-the-wire ("OTW") approach, the first section 216 can have at least one lumen instead of or in addition to an elongated member. Further details regarding catheter designs to accommodate RX and OTW configurations are discussed below with reference to FIGS. 22-34.

As shown in FIG. 1C, the second section 218 can have a lumen 206 that extends from the port 104 to the distal end 220 of the shaft 116. The lumen 206 can be configured to receive a guidewire therethrough. In some embodiments, a liner (e.g., a polymer liner) (not shown) can be formed on the inner surface of the polymer jacket 202 to limit the likelihood of the guidewire (not shown) penetrating the polymer jacket 202 and disrupting the TC assemblies 204.

In some embodiments, the outer diameter of the second section 218 can be larger than the outer diameter of the first section 216 (for example, to accommodate a guidewire). In such embodiments, the elongated shaft 116 can have a tapered shape in a proximal direction and/or include a gradual or abrupt step up in outer diameter between the first and second sections 216, 218. In other embodiments, the second section 218 can have an outer diameter that is smaller than or equal to the outer diameter of the first section 216.

Referring back to FIG. 1A, the energy generator 132 can be configured to generate a selected form and/or magnitude of energy for delivery to the treatment site via the electrodes 106. For example, in a particular embodiment, the energy generator 132 can include an energy source (not shown) operably coupled to one or more electrodes 106 and configured to generate radiofrequency (RF) energy (monopolar or bipolar). In some embodiments, the RF energy may be pulsed RF energy. In other embodiments, however, the energy generator 132 may be configured to generate microwave energy, optical energy, ultrasound energy (e.g., intravascularly delivered ultrasound, high-intensity focused ultrasound (HIFU)), direct heat energy, radiation (e.g., infrared, visible, gamma), or another suitable type of energy.

The energy generator 132 may also be configured to control, monitor, supply, or otherwise support operation of the catheter 110. For example, a control mechanism, such as foot pedal 144, may be connected (e.g., pneumatically connected or electrically connected) to the energy generator 132 to allow an operator to initiate, terminate and/or adjust various operational characteristics of the energy generator, such as power delivery. In some embodiments, for example, the energy generator 132 may be configured to provide delivery of a monopolar electric field via the electrode(s) 106. In such embodiments, a neutral or dispersive electrode 142 may be electrically connected to the energy generator 132 and attached to the exterior of the patient (not shown). In some embodiments, instead of or in addition to the electrodes 106, the distal portion 118 of the elongated shaft 116 can have ports or other substance delivery features to produce chemically based neuromodulation by delivering one or more chemicals. For example, suitable chemicals include guanethidine, ethanol, phenol, a neurotoxin (e.g., vincristine), or other suitable agents selected to alter, damage, or disrupt nerves. In certain embodiments, a combination of chemicals may be used.

In some embodiments, the system 100 includes a remote control device (not shown) configured to be sterilized to facilitate its use within a sterile field. The remote control device can be configured to control operation of the electrodes 106, the energy generator 132, and/or other suitable components of the system 100. For example, the remote control device can be configured to allow for selective activation of the electrodes 106. In other embodiments, the remote control device may be omitted and its functionality may be incorporated into the handle 112 or energy generator 132.

As shown in FIG. 1A, the energy generator 132 can further include an indicator or display screen 136. The energy generator 132 can include other indicators, including one or more LEDs, a device configured to produce an audible indication, and/or other suitable communicative devices. In the embodiment shown in FIG. 1A, for example, the display 136 includes a user interface configured to receive information or instructions from a user and/or provide feedback to the user. For example, the energy generator 132 can be configured to provide feedback to an operator before, during, and/or after a treatment procedure via the display 136. The feedback can be based on output from one or sensors (not shown) associated with the distal portion 118 of the elongated shaft 116 such as temperature sensor(s), impedance sensor(s), current sensor(s), voltage sensor(s), flow sensor(s), chemical sensor(s), ultrasound sensor(s), optical sensor(s), pressure sensor(s) and/or other sensing devices.

The system 100 can further include a controller 146 having, for example, memory (not shown) and processing circuitry (not shown). The memory and storage devices are computer-readable storage media that may be encoded with non-transitory, computer-executable instructions such as diagnostic algorithm(s) 133, evaluation/feedback algorithm(s) 138, and/or control algorithm(s) 140. The control algorithms 140 can be executed on a processor (not shown) of the system 100 to control energy delivery to the electrode(s) 106. In some embodiments, selection of one or more parameters of an automated control algorithm 140 for a particular patient may be guided by diagnostic algorithm(s) 133 that measure and evaluate one or more operating parameters prior to energy delivery. The diagnostic algorithm(s) 133 provide patient-specific feedback to the clinician prior to activating the electrode(s) 106 that can be used to select an appropriate control algorithm 140 and/or modify the control algorithm 140 to increase the likelihood of efficacious neuromodulation.

Although the controller 146 is incorporated into the energy generator 132 in the embodiment shown in FIG. 1A, in other embodiments the controller 146 may be an entity distinct from the energy generator 132. For example, additionally or alternatively, the controller 146 can be a personal computer(s), server computer(s), handheld or laptop device(s), multiprocessor system(s), microprocessor-based system(s), programmable consumer electronic(s), digital camera(s), network PC(s), minicomputer(s), mainframe computer(s), and/or any suitable computing environment.

II. Select Embodiments of Catheter Devices

A. Elongated Shaft Composition and Structure

FIG. 2A is a side view of the catheter 110 with the distal portion 118 of the shaft 116 in a low-profile or delivery state, and FIGS. 2B and 2C are enlarged views of various portions of the elongated shaft 116 shown in FIG. 2A. Referring to FIGS. 2A-2C together, the shaft 116 can be an elongated tubular member formed of a braid 205 at least partially embedded within a polymer jacket 202. The braid 205, for example, can include four TC assemblies 204 (labeled individually as TC assemblies 204a-d) intertwined with a braiding element 214. Although the braid 205 is shown having five components in FIGS. 2A-2C (four TC assemblies 204 and one braiding element 214), in some embodiments the braid 205 can have more or fewer than five components. A proximal portion of each TC assembly 204a-d is electrically connected to the handle 112 (described in greater detail below with reference to FIGS. 35A-37B), and a distal portion of each TC assembly 204a-d is electrically connected to a corresponding electrode 106a-d carried by the shaft 116 (described in greater detail below with reference to FIGS. 13-21). As such, the TC assemblies 204a-d are individually configured to measure temperature at or near its corresponding electrode 106a-d.

Each TC assembly 204a-d can include a first wire 210 (labeled individually 210a-d) and a second wire 212 (labeled individually 212a-d) made of dissimilar metals. As best seen in FIG. 2B, the first and second wires 210a-d, 212a-d can wrap around a circumference of the shaft 116 and can be arranged generally parallel to one another. Each TC assembly 204a-d can be physically and electrically isolated from the other TC assemblies 204a-d along the elongated shaft 116 between the proximal portion and the distal portion. In some embodiments, the first wires 210a-d can be made of constantan and the second wires 212a-d can be made of copper (or vice versa) such that each TC assembly 204 is configured to form a T-type thermocouple. In other embodiments, however, other types of thermocouples may be used and/or the first and/or second wires 210, 212 may be composed of other materials. Although the braid 205 is shown having four TC assemblies 204a-d, in other embodiments the braid 205 can include more or fewer than four TC assemblies (e.g., one, two, three, five, etc.).

Although the braid 205 is shown having a single braiding element 214, in other embodiments the braid 205 can include more than one braiding element (e.g., two, three, five, etc.) having the same or different size and/or or structure, and/or made of the same or different materials. In some embodiments, the braid 205 may not include any braiding element. The braiding element 214 can comprise a polymer material, such as a monofilament polymer strand or a multifilament polymer strand. Additionally, the braiding element 214 may comprise a metal. For example, the braiding element 214 can be a metal or other material having shape-memory properties corresponding to temperature thresholds (e.g., polyethylene terephthalate (PET), polyethylene naphthalate (PEN), PEN-PET, etc.). As discussed in further detail below with reference to FIGS. 5-8, all or a portion of the braiding element 214 can be heat set to a desired shape (e.g., a helical/spiral configuration) such that the braiding element is configured to impart a desired expanded configuration upon the elongated shaft 116 and/or enhance the spiral/helical memory of the shaft.

As shown in FIG. 2B, the braiding element 214 and the TC assemblies 204a-d can be intertwined and/or braided together along the length of the shaft 116. The braiding element 214 can be positioned above 230 and below 232 the adjacent TC wire 210/212 at alternating intersections between the TC wire 210/212 and the braiding element 214. For example, the braiding element 214 and the first wire 210d can have a "2 under, 2 over" configuration whereby the braiding element 214 crosses the first wire 210d on the radially interior side of the first wire 210 ("under") at two successive intersections, crosses on the radially exterior side of the second wire ("over") at the following two successive intersections, and continues this pattern for all or a portion of the length of the shaft 116. In other embodiments, the braiding element 214 may be arranged to cross over one or both wires 210, 212, cross under one or both wires 210, 212, and/or cross according to other patterns (e.g., "1 over, 1 under," "3 over, 3 under," etc.). Additionally, the braiding element 214 and the TC assemblies 204a-d can wrap around the shaft 116 in opposing directions (FIG. 2B) or the same direction (see, for example, FIG. 3). In some embodiments, the TC assemblies 204a-d and the braiding element 214 wrap around the shaft 116 but do not cross over the longitudinal axis of one another (see, for example, FIG. 3). In yet other embodiments, the shaft 116 does not include any braiding element and the shaft 116 comprises only the polymer jacket 202 and the TC assemblies 204 (see, for example, FIG. 4). A person of ordinary skill in the art will understand that the shaft 116 can have other configurations and/or can include additional or fewer braid 205 components.

Referring still to FIG. 2B, the braid 205 can have a pitch P (i.e., the longitudinal distance required for one revolution of a given TC assembly 204a-d) that can be generally constant along the length of the shaft 116. In other embodiments, the pitch P can be vary along the length of the shaft 116. For example, the braid 205 can have a tighter pitch P at a distal region of the shaft 116 for increased flexibility, and a wider pitch P at a proximal region for increased rigidity. Likewise, the PPI of the shaft 116 (i.e., longitudinal distance between successive wires) can be similarly selected to impart desired flexibility and/or rigidity along at least a portion of the shaft 116. As discussed in greater detail below with reference to FIGS. 17-22, the braid pitch P can be selected to achieve a desired spacing between adjacent electrodes along the shaft 116.

FIG. 5A is a side view of the distal portion 118 of the shaft 116 in an expanded or deployed configuration, and FIG. 5B is a cross-sectional end view taken along line 5B-5B in FIG. 5A. Referring to FIGS. 5A-5B together, in the expanded or deployed configuration, the distal portion 118 of the shaft 116 can have a generally helical/spiral shape. The distal portion 118 of the shaft 116 can include a tubular, elongated shape-memory core (e.g., Nitinol) 502 disposed within the lumen 206 of the polymer jacket 202. During manufacturing, the core 502 can be heat set on a mandrel 602 after being assembled into the shaft 116, or in other embodiments (not shown), the core can be heat set prior to placement within the lumen 206.

Figure 7:
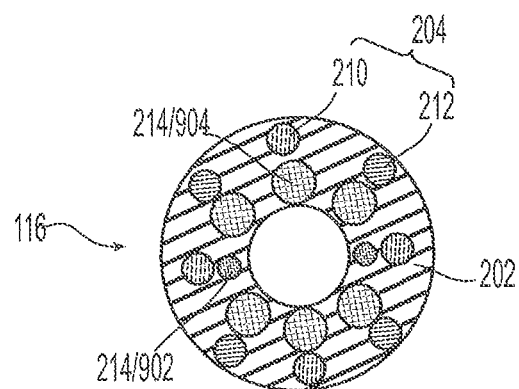
FIGS. 7-8 are cross-sectional end views of a shaft showing various braid configurations, the braid configured in accordance with the present technology.
Figure 8:
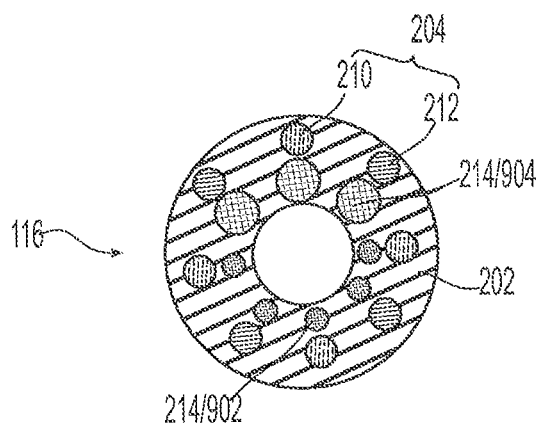

Instead of or in addition to the core 502, the braid 205 can include one or more braiding element(s) 214 composed of a shape-memory material such as Nitinol, polymer strands with a glass transition temperature greater than about 60° C., and the like. The positioning, cross-sectional area and/or composition of any or all of the braid 205 components can be manipulated to impart a desired helical/spiral shape on the expanded distal section 118. For example, in some embodiments the shaft 116 can include a mixture of large and small braiding element(s) 214. As shown in FIG. 7, the shaft 116 can include a plurality of large braiding elements 904 having a first grouping positioned on one side of the shaft 116 and a second grouping positioned on the opposite side of the shaft 116. The smaller braiding elements 902 can be positioned between the two groupings. As shown in FIG. 8, in some embodiments the shaft 116 can include a grouping of large braiding elements 904 positioned on one side of the shaft 116 and a grouping of small braiding elements 902 positioned on the opposite side of the shaft 116. In other embodiments, the shaft 116 can include other patterns and/or configurations of braiding elements 214. Likewise, the shaft 116 can include multiple braiding elements 214 made of the same or different materials.

Figure 9:
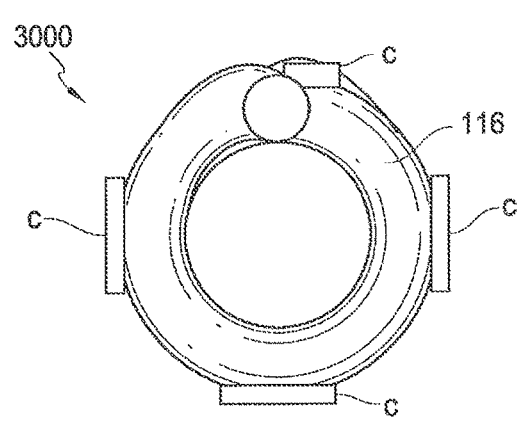
FIG. 9 is an end view showing an axial profile of a shaft in an expanded configuration, the shaft configured in accordance with the present technology.
Figure 10:
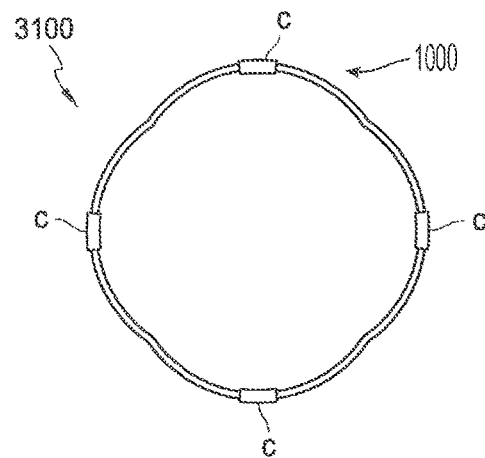
FIGS. 10-12 are schematic end views showing various axial profiles of shafts, each in an expanded configuration and configured in accordance with the present technology.
Figure 11:
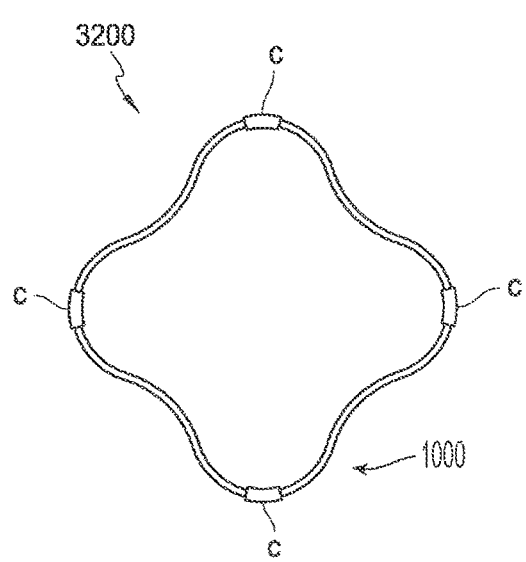
Figure 12:
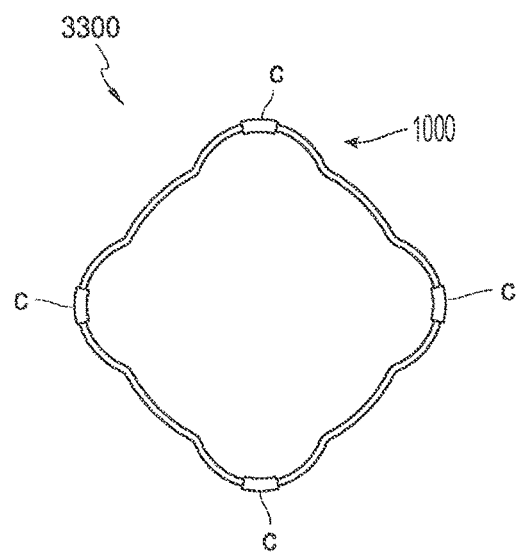

FIG. 9 is a schematic, axial view of the shaft 116 in the expanded configuration showing the desired contact pattern (denoted by contact points c) between electrodes and the vessel wall (not shown). During energy delivery via the electrodes, it can be advantageous to have the electrodes positioned on the shaft 116 such that, when the distal portion 118 is in the helical/spiral expanded configuration, the electrodes are evenly distributed about the circumference of the helix/spiral shape and therefore evenly distributed about the circumference of the vessel. In some embodiments, it can be advantageous to have each electrode 106 in a separate quadrant. Moreover, as shown in FIGS. 10-11, in some embodiments the shaft 116 can include one or more bumps 1000 protruding radially outwardly from the circumference of the shaft 116. The bumps 1000 can correspond to the contact points c and increase the contact force between the electrodes and the vessel wall.

B. Electrodes

1. Electrode Connectivity

Figure 13:
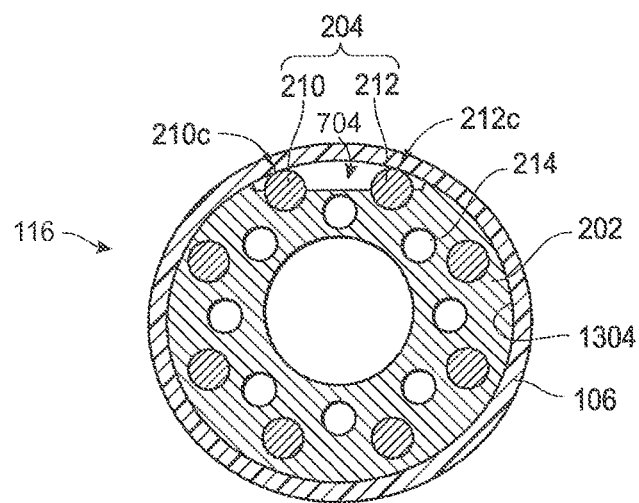
FIG. 13 is a cross-sectional end view of the shaft shown in FIG. 2C taken along line 13-13.

FIG. 13 is a cross-sectional end view of the shaft 116 in FIG. 2C taken along line 13-13. Referring to FIGS. 2B and 13 together, the electrodes 106 can be separate band electrodes (labeled individually as electrodes 106a-d) axially spaced apart along the distal portion 118 of the shaft 116. The body of each electrode 106-d surrounds the shaft 116 and at least a portion of an inner surface 1304 of each electrode 106a-d contacts the polymer jacket 202. Additionally, at least a portion of each electrode 106a-d contacts its corresponding TC assembly 204a-d (e.g., at 210c and 212c, respectively). For example, if TC assembly 204a corresponds to electrode 106a, an inner surface 1304 of the electrode 106a contacts at least a portion of each of the first and second wires 210a, 212a. Because the first and second wires 210, 212 run parallel to each other and are separated by a generally constant distance along their lengths, the portion of the first wire 210 in contact with the electrode 106 can be separated from the portion of the second wire 212 in contact with the electrode 106 along the inner surface 1304 of the electrode 106. Typical thermocouples require a junction between the two wires at the measuring end of the thermocouple. The electrode 106 (which may comprise one or more metals such as gold) may be used to efficiently transfer current between two separated wire contacts. As such, the distance between the wires 210, 212 may have a negligible effect on the accuracy of the measured temperature. As a result, the first and second wires 210, 212 can be configured to measure a temperature at or near the electrode 106.

Figure 14:
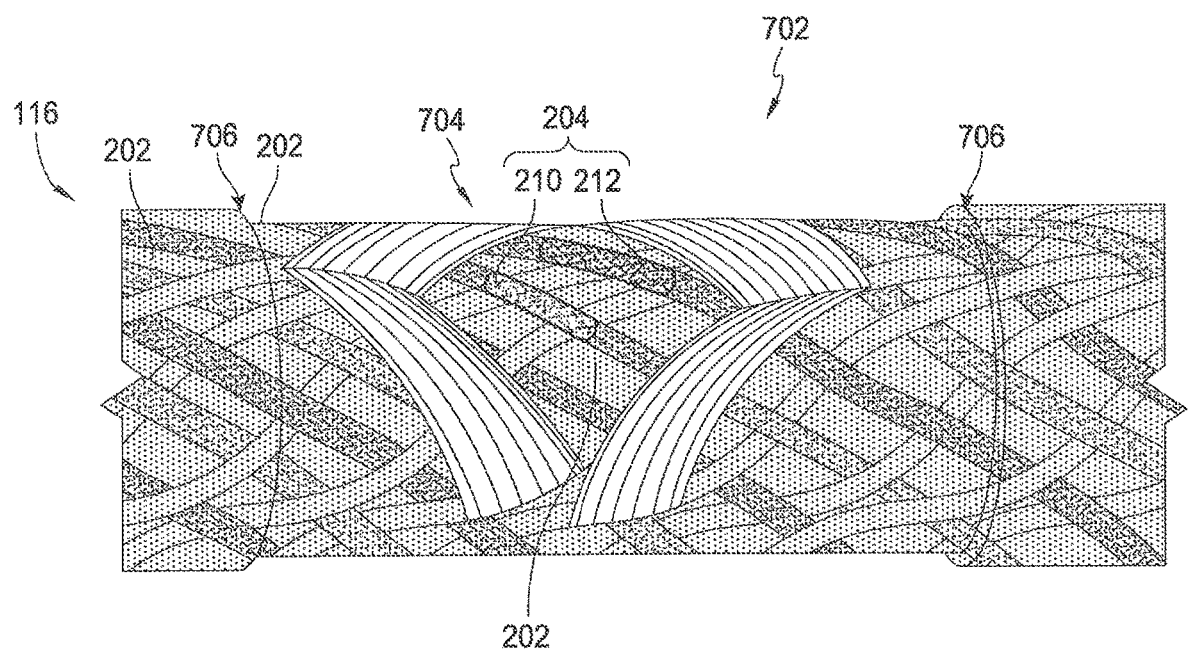
FIG. 14 is an enlarged, side perspective view of the shaft shown in FIG. 2B with the electrode removed for purposes of illustration.
Figure 15:
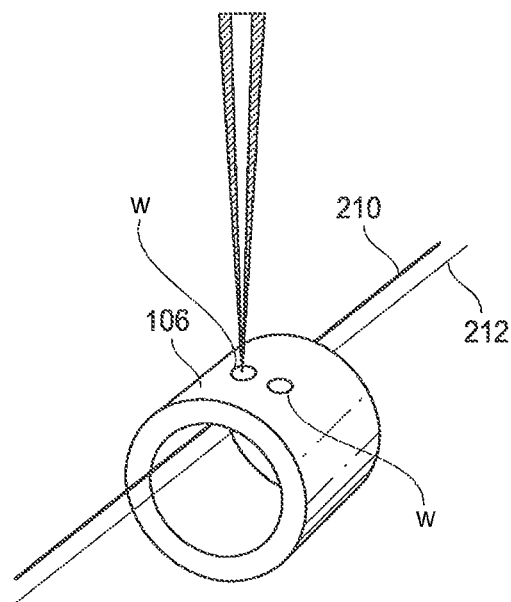
FIG. 15 is a schematic representation depicting the welding of an electrode to a TC assembly in accordance with an embodiment of the present technology.

FIG. 14 shows a portion of the shaft 116 with the electrode 106 removed for purposes of illustration. To optimize contact between the electrode 106 and the TC assemblies 204, the shaft 116 can include a notch 702 extending around its circumference that corresponds to the placement of the electrode 106. During manufacturing an additional portion of the polymer jacket 202 within the notch 702 can be removed (e.g., via laser ablation or other suitable methods) to form a recessed portion 704. As shown in FIG. 14, the recessed portion 704 can form a diamond shaped groove within a portion of the notch 702 that exposes a portion of the first and second wires 210, 212 of the targeted TC assembly 204a-d. As such, within the recessed portion 704, the polymer jacket 202 can surround a radially interior portion of the wires 210, 212 such that the polymer jacket 202 intersects the body of the wires 210, 212 at the exposed portions. In the embodiment shown in FIGS. 13 and 14, the recessed portion 704 extends toward the interior of the polymer jacket 202 to a radial distance (measured from the center of the lumen 206) generally equivalent to the radial distance between the center of one or both the wires 210, 212 and the center of the lumen 206.

It will be appreciated that the notch 702 and/or recessed portion 704 can have other shapes and/or configurations. For example, in some embodiments the notch 702 can extend around only a portion of the circumference of the shaft 116. In the embodiment shown in FIG. 14, a periphery 706 of the notch 702 is generally linear. In other embodiments, at least a portion of the periphery 706 of the notch 702 can be non-linear (e.g., sinusoidal, zig-zag, etc.). In certain embodiments, the shaft 116 does not have any notches and the recessed portion 704 is formed on the exterior surface of the shaft 116. Moreover, the recessed portion 704 can be formed in any suitable shape (e.g., circle, square, star-shaped, etc.).

To electrically couple the individual electrodes 106a-d to their respective TC assemblies 204a-d, each electrode 106a-d can be placed around the shaft 116 and positioned within its respective notch 704. All or a portion of the electrode 106 can then be swaged such that an inner surface 1304 of the electrode 106 is urged nearer and/or forced into contact with the exposed portions of the first and second wires 210, 212. As shown schematically in FIG. 15, once properly positioned and swaged, each electrode 106 can be welded to the corresponding exposed portions of the wires 210, 212 at weld points w. In other embodiments, however, other suitable techniques may be used to couple the electrodes 106 to wires 210, 212. As discussed in greater detail below, in some embodiments it may be advantageous to perform the welding at a generally central location on the electrode 106 to avoid deterioration of the electrode material at the periphery.

Figure 16:
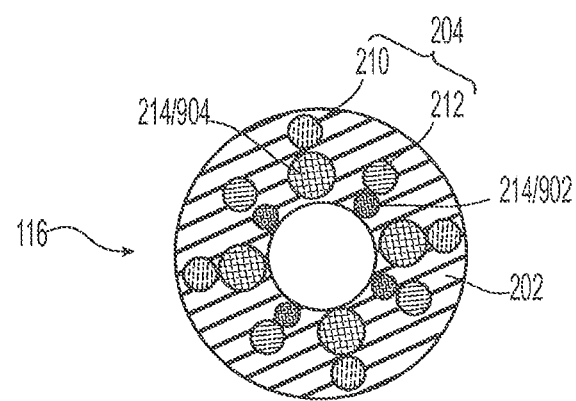
FIG. 16 is a cross-sectional end view of a shaft having braiding elements with varying cross-sectional areas configured in accordance with an embodiment of the present technology.

Several techniques can be utilized to enhance the electrical and/or mechanical connection between the electrodes 106 and the wires 210, 212. For example, to enhance the bond between the inner surface of the electrode 106 and the first and second wires 210, 212, a conductive filler (not shown) may be injected into the recessed portion 704 instead of or in addition to welding. Also, to increase the surface contact between the electrodes and the first and second wires 210, 212, the positioning, cross-sectional area and/or composition of any or all of the braid 205 components can be manipulated to selectively position the wires 210, 212 near the outer surface of the polymer jacket 202. For example, the diameter of the braiding element 214 and the positioning of the braiding element 214 (relative to the first and/or second wires 210, 212) can be selected to affect the positioning of the first and/or second wires 210, 212. As shown in FIG. 16, for example, the shaft 116 can include at least one braiding element 214 having a larger cross-sectional area 904 positioned radially inferior to the first wire 210 and/or second wire 212. The larger braiding element 904 is expected to help position the first and/or second wires 210, 212 closer to an outer surface of the polymer jacket 202. In a similar fashion, the selection of a monofilament or multifilament braiding element can affect electrode positioning. Likewise, braiding elements having circular cross-sectional areas can urge the first and/or second wires 210, 212 radially outwardly, while braiding elements having flattened cross-sectional areas (e.g., rectangle, ellipsis, etc.) may take up less radial space in the polymer jacket 202. Any or the above-referenced techniques can be utilized in any combination.

2. Electrode Spacing Algorithms

For efficacious treatment, it can be advantageous to create a fully-circumferential lesion along a length of the target blood vessel. For example, distal portion 118 can be configured to form a lesion or series of lesions (e.g., a helical spiral lesion or a discontinuous lesion) that is fully-circumferential overall, but generally non-circumferential at longitudinal segments of the treatment location. As discussed above with reference to FIG. 2A and FIG. 9, the electrodes 106 can be positioned along the distal portion 118 of the shaft 116 such that, when the shaft 116 is in the expanded configuration, the electrodes are evenly distributed about the circumference of the helix/spiral shape into four quadrants. As demonstrated by FIG. 17, the distance ES between adjacent electrodes along the shaft 116 can be selected to achieve such a circumferential distribution of electrodes in the expanded configuration. For example, for vessel diameters between about 3 mm and about 8 mm, the distance ES between adjacent electrodes along the shaft 116 can be about 7.5 mm. In other embodiments, however, the electrode spacing ES may vary.

Because of the braided and/or wrapped configuration of the wires 210, 212 along the length of the shaft 116, several parameters must be considered in order to achieve a desired electrode spacing ES. For example, the distance d between adjacent wires, the size of the band electrodes, and the welding parameters can affect the electrode spacing ES. To illustrate this concept, FIG. 18 shows a section of the distal portion 118 of the shaft 116 that includes first, second, third and fourth TC assemblies 204a-d wrapped around the shaft 116 and first and second electrodes 106a, 106b (shown schematically) welded to first and second TC assemblies at weld points 1202a and 1202b, respectively. If the distance d between adjacent wires is too small (i.e., the wires are wound very close together), the weld points of a particular electrode will be too close together and may overlap. If the distance d is too large (i.e., the wires are wound too far apart), one or both of the weld points may be too close to the perimeter of the electrode which can lead to a poor weld (e.g., not enough metal for the weld to be effective). Accordingly, it can be advantageous to have the weld points spaced apart at a central portion of the electrode, as shown in FIG. 18. Additionally, it can be advantageous to form the weld points in a single plane (e.g., for ease of manufacturing).

FIG. 19 is a table showing ABCD-patterned electrode spacing arrangements, and FIG. 20 is a table showing ADCB-patterned electrode spacing arrangements. The letters "A," "B," "C," and "D" each represent a corresponding TC assembly 204a-d shown in FIGS. 17 and 18, and each row illustrates a different spacing between TC assembly welding points. Because each TC assembly 204a-d can only be coupled to a single electrode, in each row only one of "A," "B," "C," and "D" are surrounded by a box (which denotes the portion of the TC assembly to be coupled to its corresponding electrode). The first row of FIG. 19, for example, denotes a configuration where the electrodes are welded to successive, immediately adjacent portions of TC assemblies 204a-d. In such a configuration, there are "two steps" between welding points (denoted by the far right column). "Two steps," as used herein, denotes one move from a TC assembly with weld points to the next TC assembly with weld points ("two steps" because each wire counts as a step, and each TC assembly can include two wires). In the second row of FIG. 19, the weld points skip the immediately adjacent TC assembly and are located instead on the next occurring TC assembly (10 steps). Such a pattern continues in the rest of FIG. 19 and FIG. 20.

Based on the steps shown in the exemplary ABCD and ADCB patterns in FIGS. 19 and 20, a desired braid density PPI ("picks per inch") can be determined by plugging the steps and desired distance d between electrodes into the following equations:

Electrode Positioning Error $E$=electrode spacing ES$-$(steps*$d$);

Distance $d$ between adjacent wires (in mm)=25.4/PPI mm; and

Electrode Positioning Error $E$=electrode spacing ES$-$(steps*(25.4/PPI mm)).

FIG. 21 is a graph showing PPI versus electrode position error E for an electrode spacing ES of 7.5 mm. As used herein with reference to FIG. 21, "error" refers to the absolute difference between the actual electrode spacing and the desired electrode spacing (e.g., 7.5 mm). On the graph shown in FIG. 21, for the ABCD pattern, the electrode positioning error E is lowest at around 34 PPI and 48 PPI, and for the ADCB pattern, at around 61 PPI and 74 PPI. Depending on the desired electrode spacing ES and the size of the electrodes, however, one or more of these PPI values may still be undesirable. For example, 34 PPI may still be result in distance between adjacent wires being too large, and 74 PPI may still result in the distance between adjacent wires being too small. Accordingly, in other embodiments, other suitable arrangements and/or spacings may be utilized.

C. Select Embodiments of Guidewire Accommodations

1. Rapid Exchange Port Embodiments

Figure 22:
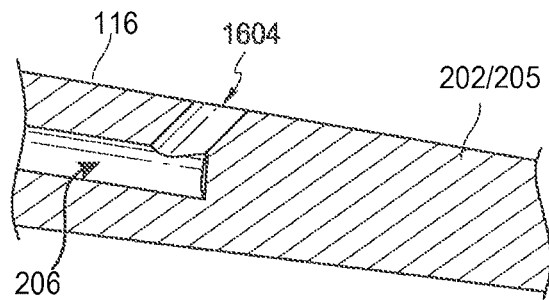
FIGS. 22-23 are side views of a shaft shown during various stages of manufacturing a rapid exchange port configured in accordance with an embodiment of the present technology.
Figure 23:
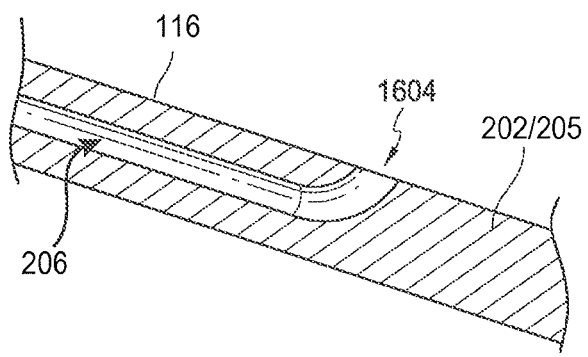
Figure 24:
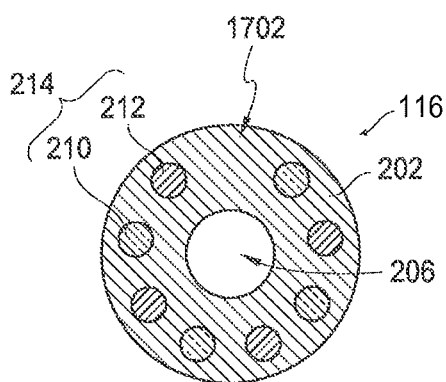
FIG. 24 is a cross-sectional end view of a shaft having a port section configured in accordance with an embodiment of the present technology.

As discussed above with reference to FIGS. 1A-1C, the elongated shaft 116 can include a port 104 configured to receive a guidewire in a rapid-exchange configuration. Referring now to FIG. 22, the lumen 206 of the shaft 116 can have an angled portion that extends radially outwardly in a distal direction towards the exterior shaft 116. The angled portion can be formed by molding the polymer jacket around a mandrel or by other suitable methods (e.g., a femtosecond laser, drilling, ablation, etc.). An opening 1604 in the shaft 116 can be made by removing a portion of the braid 205 and/or polymer jacket 202 at a location along the shaft 116 corresponding to the desired position of the port 1604. As shown in FIG. 23, the polymer jacket 202 can be heated to soften the polymer 202 and reflow the polymer material so as to smooth the transition between the port 1604 and the lumen 206. Additionally, FIG. 24 is a cross-sectional end view of one embodiment of a shaft 116 having a non-braided portion 1702 reserved for formation of a rapid-exchange port.

Figure 25:
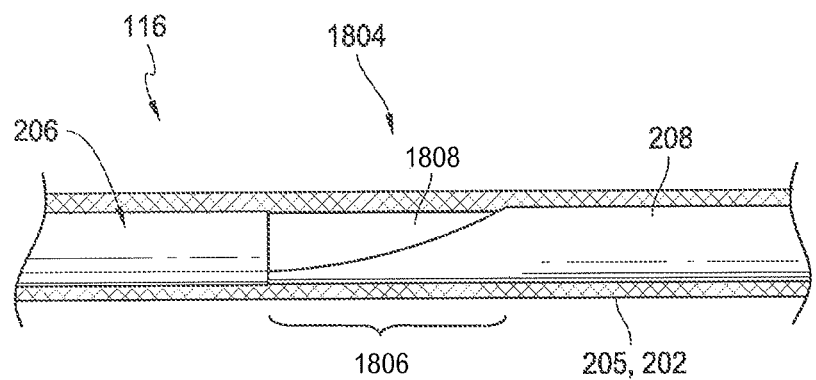
FIG. 25 is a side view of a shaft with a portion of the braid removed for purposes of illustration, the shaft shown during a stage of manufacturing and configured in accordance with an embodiment of the present technology.

FIG. 25 is a side view of a shaft 116 during a stage of manufacturing in accordance with an embodiment of the present technology. As shown in FIG. 25, a proximal portion of the shaft 116 can include an elongated member 208 and a distal portion of the shaft can include a lumen 206. The elongated member 208 can include a tapered distal portion 1806. A polymer fill 1808 can abut a tapering surface of the distal portion 1806 and define the area between the braid/polymer jacket 202, 205, the lumen 206, and distal portion 1806. The polymer fill 1808 can be made of the same polymer used for the polymer jacket 202 and/or a different polymer. A portion of the braid/polymer jacket 205, 202 and a portion of the polymer fill 1808 between the tapering surface can be removed to form the port (generally at location 1804) by ablation, drilling, or other suitable methods.

Figure 26:
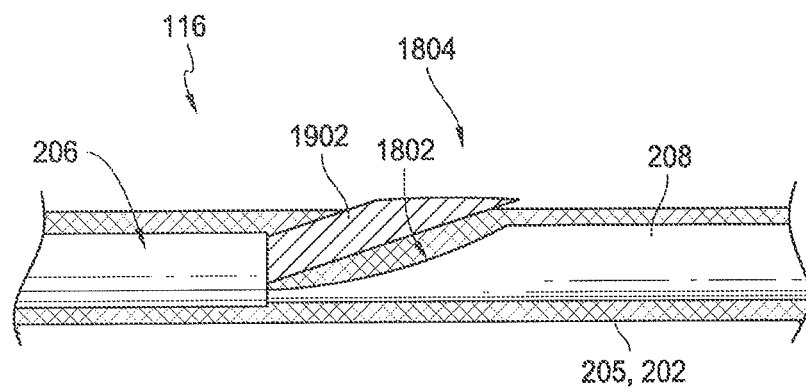
FIG. 26 is a side view of a shaft with a portion of the braid removed for purposes of illustration, the shaft shown during a stage of manufacturing and configured in accordance with an embodiment of the present technology.

FIG. 26 is a side view of a shaft 116 during a stage of manufacturing in accordance with another embodiment of the present technology. The shaft 116 can be generally similar to the shaft 116 described above with reference to FIG. 25, except instead of having a polymer fill 1808, the shaft 116 can include a plug 1902 between the tapering surface and the braid/polymer jacket exterior 202, 205. The plug 1902 can be made of a polymer (dissimilar to that used for the polymer jacket 202) or metal that can be removed once the polymer jacket 202 has been flowed over the braid 205 and set. As such, removal of the plug 1902 forms a newly made opening (generally at location 1804) that is in fluid communication with the lumen 206 at the distal portion of the shaft 116.

Figure 27:
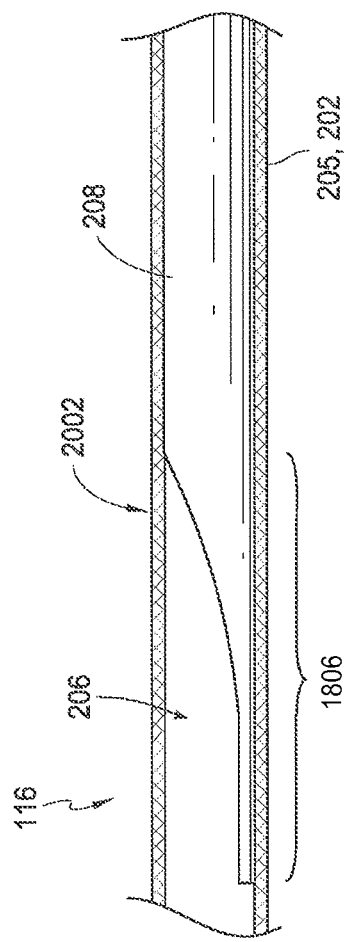
FIG. 27 is a side view of a shaft with a portion of the braid removed for purposes of illustration, the shaft shown during a stage of manufacturing and configured in accordance with an embodiment of the present technology.
Figure 29:
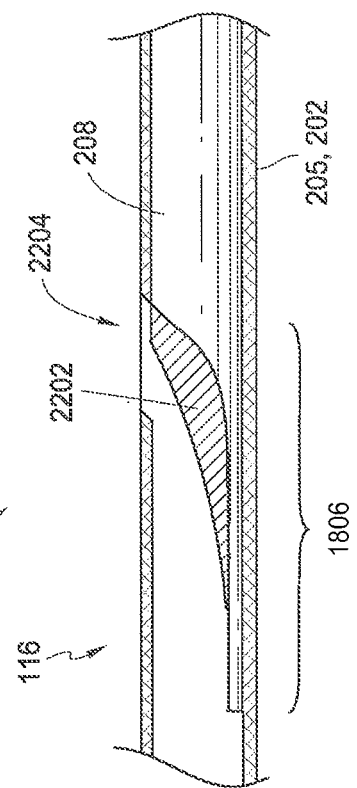
FIG. 29 is a side view of a shaft with a portion of the braid removed for purposes of illustration, the shaft shown during a stage of manufacturing and configured in accordance with an embodiment of the present technology.
Figure 28:
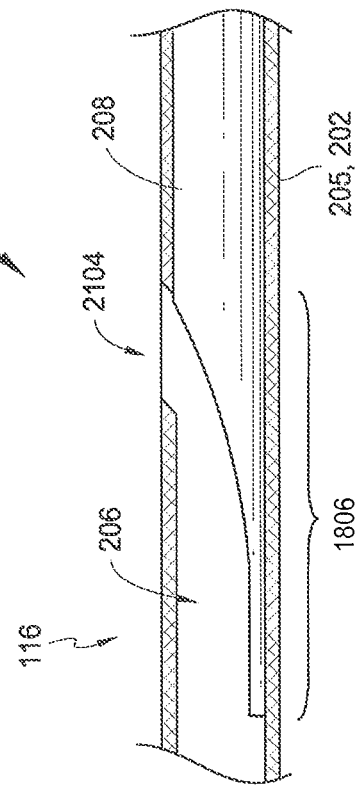
FIG. 28 is a side view of a shaft with a portion of the braid removed for purposes of illustration, the shaft shown during a stage of manufacturing and configured in accordance with an embodiment of the present technology.

FIG. 27 is a side view is a side view of a shaft 116 during a stage of manufacturing configured in accordance with another embodiment of the present technology. As shown in FIG. 27, a proximal portion of the shaft 116 can include an elongated member 208 and a distal portion of the shaft can include a lumen 206. The elongated member 208 can include a tapered distal portion 1806. As shown in FIGS. 27-28, a portion 2002 of the braid/polymer jacket 202, 205 aligned with the tapered distal portion 1806 can be removed create an opening 2104 in the shaft 116 that is in fluid communication with the lumen 206. As shown in FIG. 29, in some embodiments a portion 2202 of the elongated member 208 can also be removed to create a smoother transition to the lumen 206.

Figure 30A:
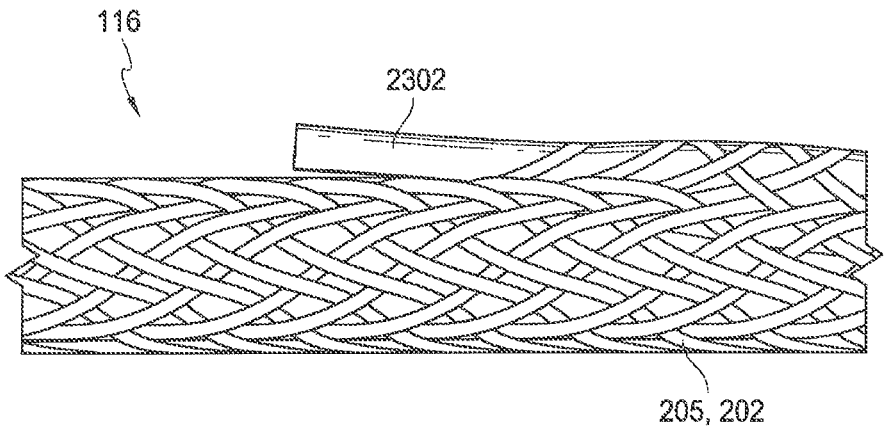
FIG. 30A is a side view of a shaft shown during a stage of manufacturing in accordance with an embodiment of the present technology.
Figure 30B:
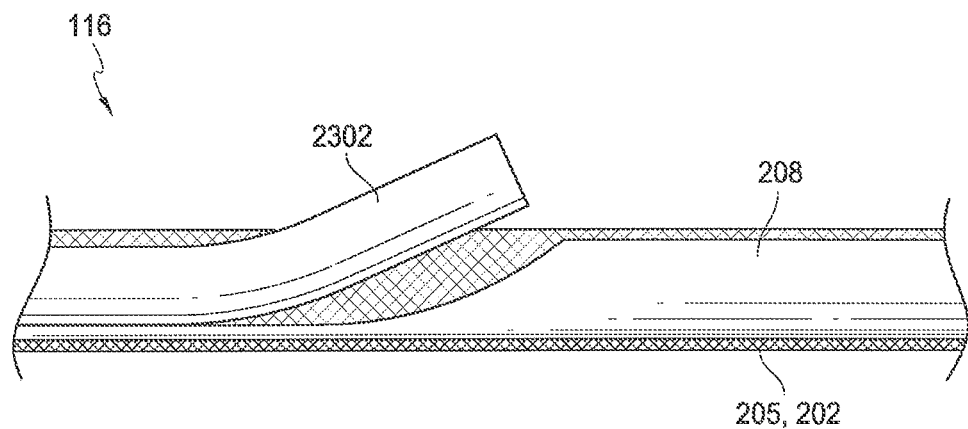
FIG. 30B is a side view of the shaft shown in FIG. 30A with a portion of the braid removed for purposes of illustration.
Figure 31:
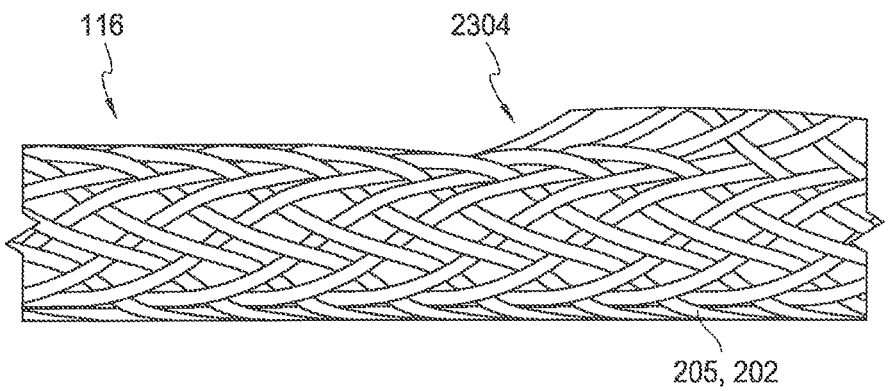
FIG. 31 is a side view of a shaft having a rapid exchange port configured in accordance with an embodiment of the present technology.

FIG. 30A is a side view of a shaft during a stage of manufacturing configured in accordance with the present technology, and FIG. 30B is an opposite side view of the shaft shown in FIG. 30A with a portion of the braid/polymer jacket 205, 202 removed for purposes of illustration. Referring to FIGS. 30A-30B together, during manufacturing the braided portion of the shaft 116 can be formed around an elongated tubular member 2302 (e.g., mandrel, hypotube, etc.) having an angled portion at a distal end. A generally linear portion of the member 2302 can be used to form the central lumen 206 (not shown) at the distal portion 118 of the shaft 116, and the angled portion can form the connection between the lumen 206 (not shown) and the opening 2304 (FIG. 31) at the exterior portion of the shaft 116. As shown in FIG. 31, once the braiding is complete and the polymer set, the member 2302 can be removed to form the opening 2304 configured to be used as a rapid exchange port.

2. Over-the-Wire ("OTW") Embodiments

Figure 32:
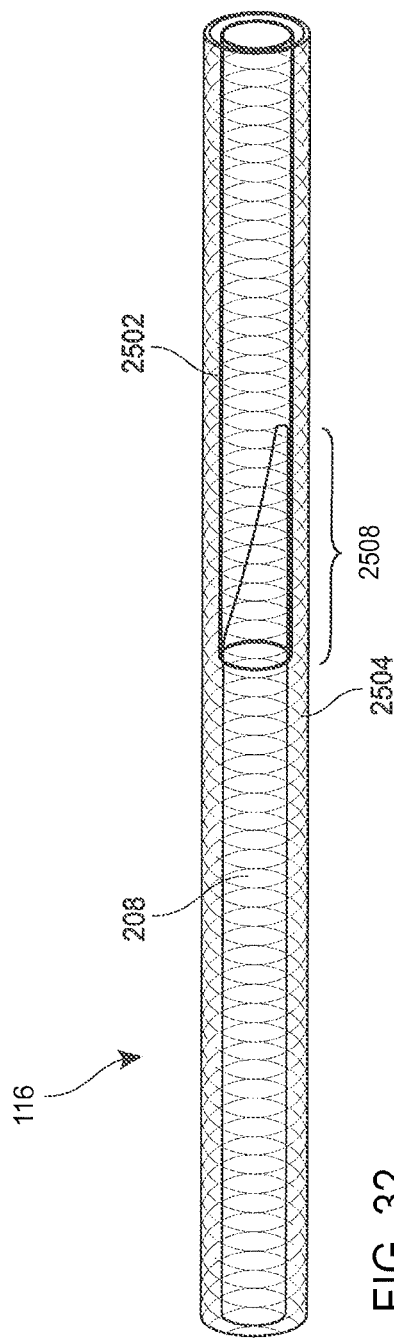
FIG. 32 is a side view of a shaft having an over-the-wire configuration, the shaft configured in accordance with an embodiment of the present technology.
Figure 33A:
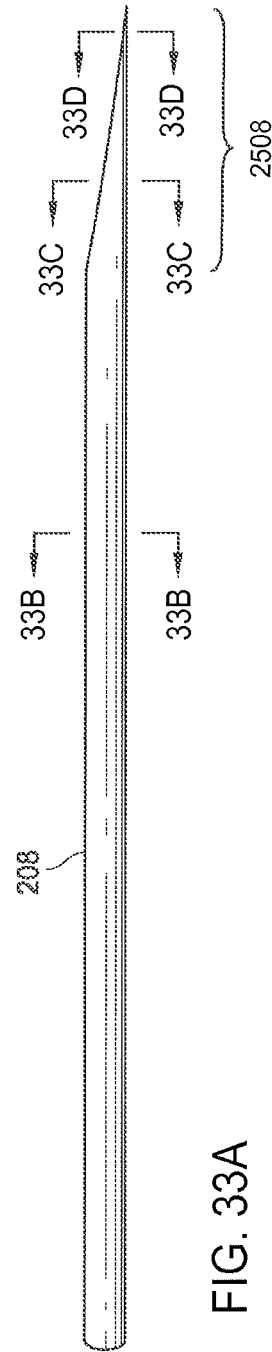
FIG. 33A is an enlarged, isolated side view of a first elongated member of the shaft shown in FIG. 32.
Figure 33D:
FIGS. 33B-33D are cross-sectional end views taken along lines 33B-33B, 33C-33C and 33D-33D in FIG. 33A, respectively.
Figure 33C:
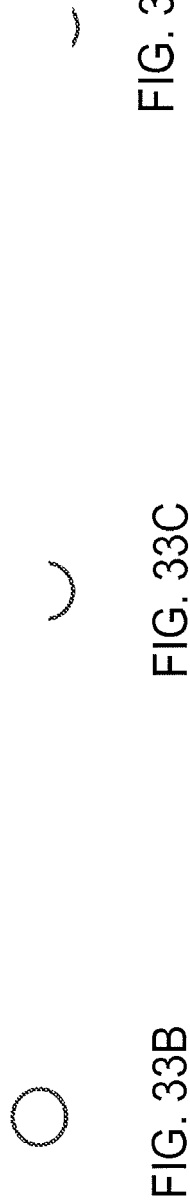
Figure 33B:
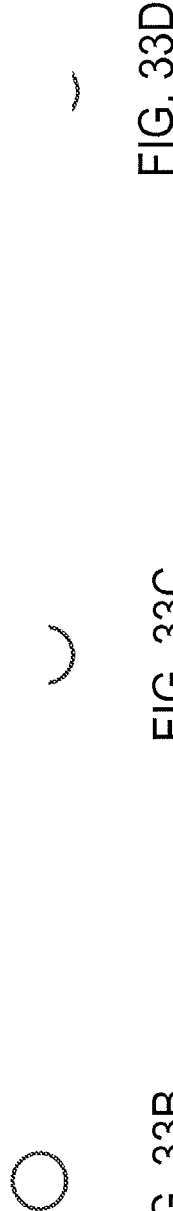

FIG. 32 shows a catheter shaft 116 configured in accordance with the present technology that is configured to receive a guidewire in an over-the-wire ("OTW") configuration. The shaft 116 can include a braid/polymer exterior 2504 surrounding a first tubular member 208, and a second tubular member 2502. As best shown in the isolated view of the first member 208 in FIG. 33A (and corresponding cross-sectional end views 33B-33D), the first member 208 can have a distal portion 2508 that tapers in the proximal to distal direction for increased flexibility and a smoother transition between the first and second members 208, 2502. A proximal portion of the second member 2502 can be positioned over the at least the distal portion 2508 of the first member 208. As such, the lumen (not shown) of the first member 208 may be contiguous with the lumen (not shown) of the second member 2502. The combined lumens of the first and second members 208, 2502 form a shaft lumen configured to receive a guidewire therethrough.

Figure 34:
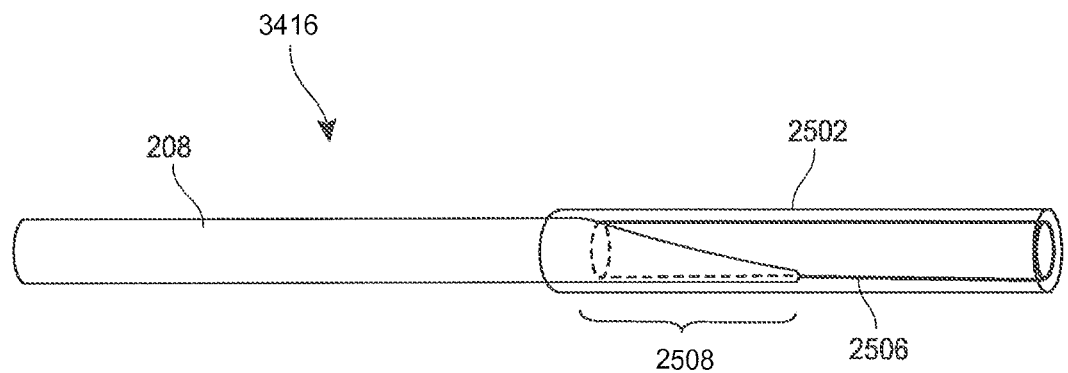
FIG. 34 is a side view of a shaft having an over-the-wire configuration configured in accordance with another embodiment of the present technology.

FIG. 34 shows another embodiment of a catheter shaft 3416 configured in accordance with the present technology that is configured to receive a guidewire in an over-the-wire ("OTW") configuration. The shaft 3416 can be generally similar to the shaft 3416 described above with reference to FIGS. 32-33D, except the shaft 3416 of FIG. 34 includes a third tubular member 2506 positioned within the tapered distal portion 2508 of the first member 208. As such, at least a portion of the third member 2506 is sandwiched between the first member 208 and the second member 2502, thereby providing increased support at the transition between the first and second members 208, 2502. In some embodiments, heat can be applied to the second and third members 2502, 2506 to increase the bond between them.

D. Select Embodiments of Handle Assemblies

Figure 35A:
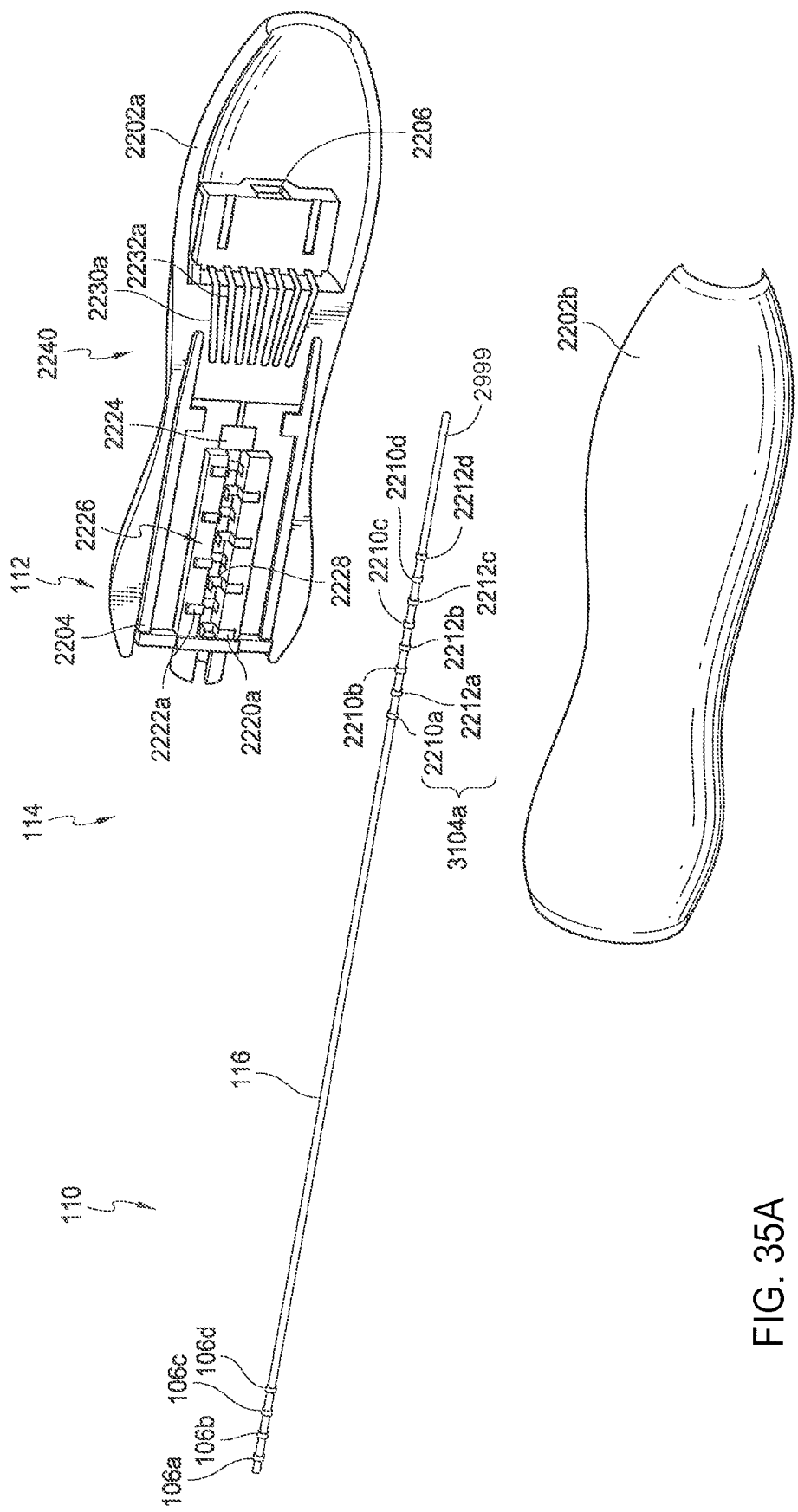
FIG. 35A is a perspective, exploded view of an embodiment of a catheter handle and shaft configured in accordance with the present technology.
Figure 35B:
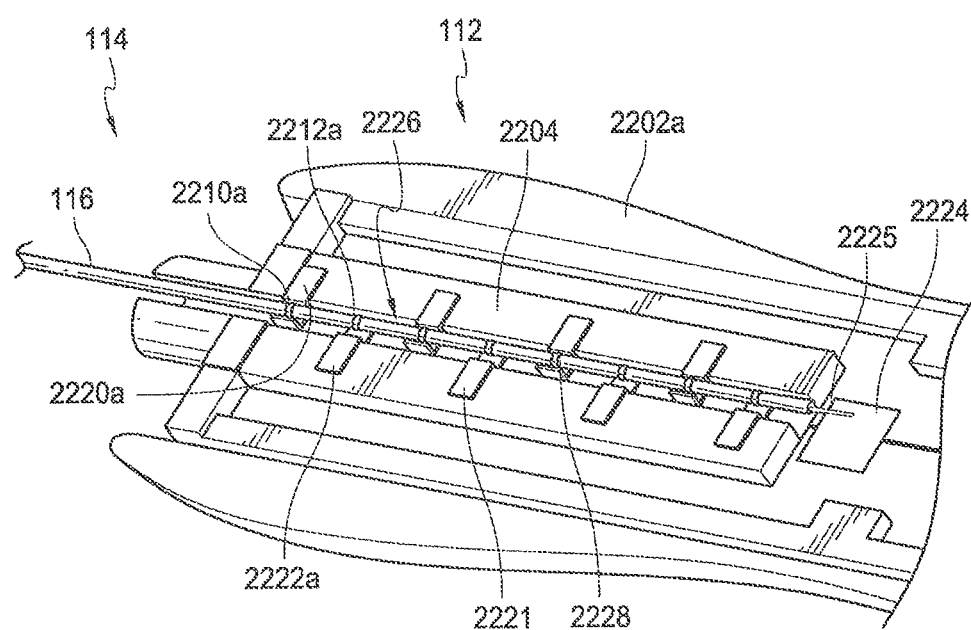
FIG. 35B is a perspective, enlarged view of the proximal portion of the catheter handle shown in FIG. 35A.

FIG. 35A is an exploded, perspective view of the catheter 110 shown in FIG. 1A, and FIG. 35B is an enlarged view of the proximal portion 114 of the shaft 116. Referring to FIGS. 35A and 35B together, a proximal portion 114 of the shaft 116 can be operably coupled to the handle 112 via a snap-fit arrangement. The proximal portion of the shaft 116, for example, may include a plurality of pairs of conductors (referred to as 3104$a$-$d$) positioned on an exterior portion of the shaft 116 and electrically coupled to the first and second wires 210, 212 of the TC assemblies 204$a$-$d$. For example, the proximal portion 114 of the shaft 116 can include four first conductors 2210 (referred to as conductors 2210$a$-$d$) electrically coupled to corresponding first wires 210, and four second conductors (referred to as conductors 2212$a$-$d$) electrically coupled to corresponding second wires 212. In other embodiments, the proximal portion 115 can include more or less than eight total conductors depending on the number of electrodes. Furthermore, one conductor (instead of a pair of conductors) could correspond to a pair of first and second wires (e.g., 210a and 212b, etc.). Although in the illustrated embodiment the conductors are shown in an order that corresponds with the electrodes (e.g., distally to proximally, "a" is most distal, "d" is most proximal), in other embodiments the conductors 2210, 2212 can have any order; the order of the conductors 3104a-d does not necessarily correspond to the order of the electrodes 106a-d.

Referring still to FIGS. 35A-35B, the handle 112 includes a housing 2202 including two complimentary halves 2202a and 2202b (only the interior of 2202a shown for ease of description). Each half includes a shaft receiving region 2204, a routing portion 2240, and connector attachment 2206. The shaft receiving region 2204 can include a longitudinal groove 2226 and a plurality of conductive pins 2220a-d and 2222a-d (collectively referred to as 2221), each having a horseshoe-shaped portion 2228 at least partially within the groove 2226. The groove 2226 can be configured to receive the proximal portion 114 of the shaft 116, and the horseshoe-shaped portion 2228 of the pins 2221 can be configured to engage at least a portion of the conductors 2220a, 2210a on the received shaft 116. When the shaft 116 is pressed into place within the groove 2226 of the receiving region 2204 (after aligning the conductors and the pins), the conductors 2220a, 2210a engage the corresponding pin 2220a-d, 2222a-d, thus electrically coupling the shaft 116 to the handle 112. The horseshoe-shaped portion 2228 initially resists the movement of the shaft into the groove; however, past a certain threshold the horseshoe-shaped portion 2228 is forced open and allows the conductor to sit within the horseshoe-shaped portion to securely hold the shaft 116 (e.g., a "snap-fit").

As best seen in FIG. 35B, once the proximal portion 114 of the shaft is in place within the receiving region 2204, the proximal tip 2225 of the shaft can be welded to a plate 2224 mounted within the housing 2202. For example, the braid 205 and polymer jacket 202 can be removed from the proximal tip of the shaft 116 (not shown), thereby exposing the mandrel 2225, which can then be welded to the plate 2224. As such, a proximal portion of the mandrel 2225 can be fixed to an interior portion of the handle 112 to improve the torque response of the shaft 116 (e.g., by reducing and/or preventing axial and rotational movement of the shaft 116 relative to the handle 112).

The conductive pins 2220a-d, 2222a-d can be electrically coupled to the routing portion 2240 (FIG. 35A) that includes a plurality of routing lines 2230a-d, 2232a-d, individually corresponding to the conductive pins 2220a-d, 2222a-d. The routing lines 2230a-d, 2232a-d are coupled to the connector attachment 2206 positioned at a proximal portion of the handle 112, as shown in FIG. 35A. The connector attachment 2206 is configured to be operably coupled with the connector 130 (see FIG. 1A) to electrically connect the handle 112 to the energy generator 132 or other component of the system.

FIG. 36A is a side view of another embodiment of a catheter 2310 configured in accordance with the present technology, and FIG. 36B is an enlarged cross-sectional view of a proximal portion 114 of the handle 2300 shown in FIG. 36A. The catheter 2310 can be generally similar to the catheter 110 described above with reference to FIGS. 1A-1C and 35A-35C except as detailed below. Referring to FIGS. 36A and 36B together, the catheter 2310 can include a handle 2300 having an interior surface with a printed circuit board ("PCB") directly printed thereon. A plurality of routing lines 2318 can extend from the PCB to a recessed receiving region 2320 at the distal end of the handle 2300. The routing lines 2318 can individually correspond to the first wire 210, the second wire 212, and/or the TC assembly 204 (FIG. 1B). A connector 2330 (FIG. 36C) can be coupled to a proximal portion of the PCB board, thereby providing the electrical connection between the handle 2300 and the energy generator 132. As shown in FIG. 36D, a portion of the proximal section of the polymer jacket 2302 can be removed to expose the proximal ends of the TC assemblies 204. As such, the exposed wires 2304 at the proximal portion of the shaft 2316 can be pressed into place in the receiving region, thus electrically coupling the shaft 116 to the handle 112. Moreover, a proximal end of the mandrel 2326 (shown schematically in FIG. 36B) can be fixed to a plate 2322 on the handle 112 to improve the torque response of the shaft 2316. In these and other embodiments, a distal portion 2324 of the handle 112 can be lengthened in a distal direction to improve the torque response of the shaft 2316, as well as increase the surface area available for a user to grip and control the handle 112.

Figure 37A:
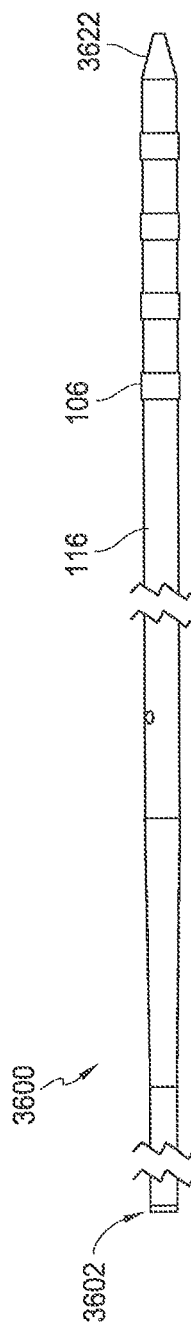
FIG. 37A is a side view of an embodiment of an elongated shaft configured in accordance with the present technology.
Figure 37B:
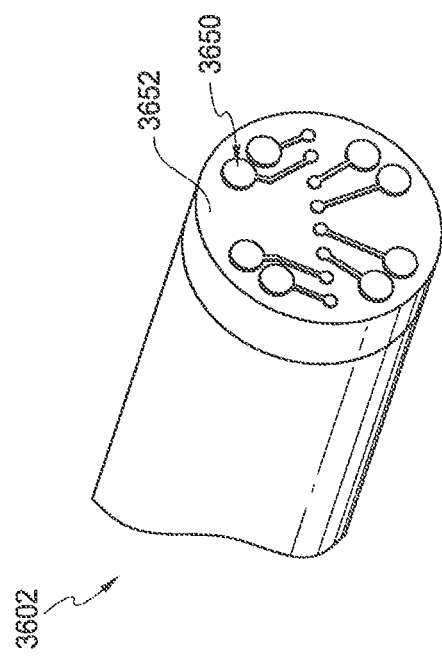
FIG. 37B is a perspective, enlarged view of a proximal portion of the shaft shown in FIG. 37A.

FIG. 37A is a side view of another embodiment of a catheter 3600 configured in accordance with the present technology, and FIG. 37B is an enlarged view of the proximal end of the catheter shaft 116 of the catheter 3600 of FIG. 37A. Referring to FIGS. 37A-37B together, the catheter 3600 can be generally similar to the catheters 110 and 2310 described above with reference to FIGS. 1A-1C, 35A-35C and 36A-36C, except that the catheter 3600 has disc-shaped connector 3652 coupled to the proximal end of the shaft 116. The connector 3652 can be electrically coupled to the TC assemblies (not shown) and provide one or more connection points 3650 at an exterior portion of the disc 3652 that correspond to the TC assemblies. A connector (not shown) can be coupled to the disc 3652 and extend between the shaft 116 and the handle 112 (FIG. 1A) and/or energy generator 132 (FIG. 1A).

III. Neuromodulation

Neuromodulation is the partial or complete incapacitation or other effective disruption of nerves innervating, for example, an organ. As an example, renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death, among others. The reduction of afferent neural signals typically contributes to the systemic reduction of sympathetic tone/drive, and renal neuromodulation is expected to be useful in treating several conditions associated with systemic sympathetic overactivity or hyperactivity. Renal neuromodulation can potentially benefit a variety of organs and bodily structures innervated by sympathetic nerves.

Thermal effects can include both thermal ablation and non-ablative thermal alteration or damage (e.g., via sustained heating and/or resistive heating) to partially or completely disrupt the ability of a nerve to transmit a signal. Desired thermal heating effects, for example, may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration. More specifically, exposure to thermal energy in excess of a body temperature of about 37° C., but below a temperature of about 45° C., may induce thermal alteration via moderate heating of target neural fibers or of vascular structures that perfuse the target fibers. In cases where vascular structures are affected, the target neural fibers may be denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures that perfuse the target fibers. In some patients, it may be desirable to achieve temperatures that thermally ablate the target neural fibers or the vascular structures, but that are less than about 90° C., or less than about 85° C., or less than about 80° C., and/or less than about 75° C. Other embodiments can include heating tissue to a variety of other suitable temperatures. Regardless of the type of heat exposure utilized to induce the thermal neuromodulation, a reduction in renal sympathetic nerve activity (RSNA) is expected.

Various techniques can be used to partially or completely incapacitate neural pathways, such as those innervating the kidneys. The purposeful application of energy (e.g., RF energy, mechanical energy, acoustic energy, electrical energy, thermal energy, etc.) to tissue and/or the purposeful removal of energy (e.g., thermal energy) from tissue can induce one or more desired thermal heating and/or cooling effects on localized regions of the tissue. The tissue, for example, can be tissue of the renal artery and adjacent regions of the renal plexus, which lay intimately within or adjacent to the adventitia of the renal artery. For example, the purposeful application and/or removal of energy can be used to achieve therapeutically effective neuromodulation along all or a portion of the renal plexus.

Many current helical or spiral neuromodulation systems deploy mainly from a distal to proximal direction. Often times the distal end of the electrode array is moveable in a proximal and distal direction but the proximal end of the electrode array is fixed relative to the catheter shaft. As a result, in vessels or portions of vessels with tapered diameters (e.g., the renal artery), many devices first deploy distally where the vessel diameter is smaller, which can prevent the electrodes at the proximal end of the helical structure from making contact with the inner vessel wall. Likewise, achieving contact with the vessel wall along a substantial length of the helical or spiral device can be difficult in vessels with tortuous or unpredictable morphologies. To address this need, the present technology provides several embodiments of devices, systems, and methods that provide bi-directional deployment of a helical or spiral device to better position the electrodes in apposition with the vessel wall.

IV. Examples

The following examples are illustrative of several embodiments of the present technology:

1. A catheter apparatus, comprising:
   an elongated tubular shaft having a proximal portion and a distal portion, wherein the elongated tubular shaft includes—
      a polymer material;
      a first thermocouple assembly wrapped about and/or embedded within the polymer material of the shaft, wherein the first thermocouple assembly comprises a first pair of wires composed of dissimilar metals;
      a second thermocouple assembly wrapped about and/or embedded within the polymer material of the shaft, wherein the second thermocouple assembly comprises a second pair of wires composed of dissimilar metals, and wherein the second pair of wires is physically and electrically isolated from the first pair of wires along the elongated shaft between the proximal portion and the distal portion;
   a first electrode at the distal portion of the elongated shaft and electrically coupled to the first thermocouple assembly;
   a second electrode at the distal portion of the elongated shaft and electrically coupled to the second thermocouple assembly,
   wherein the distal portion of the shaft and the first and second electrodes together define a therapeutic assembly adapted to be located at a target location within a blood vessel of a human patient,
   wherein the elongated shaft and the therapeutic assembly together define therethrough a guide wire lumen configured to slidably receive a medical guide wire,
   wherein axial movement of the guide wire relative to the therapeutic assembly transforms the therapeutic assembly between (a) a low-profile delivery configuration and (b) a deployed configuration having a spiral shape.

2. The catheter apparatus of example 1, further comprising:
   a third thermocouple assembly helically wrapped about and/or embedded within the polymer material of the shaft, wherein the third thermocouple assembly comprises a third pair of wires;
   a fourth thermocouple assembly helically wrapped about and/or embedded within the polymer material of the shaft, wherein the fourth thermocouple assembly comprises a fourth pair of wires;
   a third electrode at the distal portion of the elongated shaft and electrically coupled to the third thermocouple assembly; and
   a fourth electrode at the distal portion of the elongated shaft and electrically coupled to the fourth thermocouple assembly,
   wherein the first, second, third, and fourth pair of wires are all physically and electrically isolated from each other along the elongated shaft between the proximal portion and the distal portion.

3. The catheter apparatus of example 1 or example 2 wherein the first, second, third, and fourth electrodes comprise gold band electrodes.

4. The catheter apparatus of any of examples 1-3 wherein the individual electrodes are spaced apart from each other along the elongated shaft by 7.5 mm.

5. The catheter apparatus of any of examples 1-4, further comprising a handle that is coupled to the proximal portion of the elongated shaft via a snap fit arrangement.

6. The catheter apparatus of example 5 wherein the proximal portion of the handle comprises four contacts arranged thereon and in electrical contact with corresponding individual wires of the first and second thermocouple assemblies, and wherein the contacts are positioned to mate with corresponding pins carried by the handle when the proximal portion of the shaft is coupled with the handle in a snap fit arrangement.

7. The catheter apparatus of example 6 wherein the contacts are gold contacts.

8. The catheter apparatus of any of examples 1-7, further comprising a rapid exchange port positioned along the shaft between the proximal portion and the distal portion of the shaft and in communication with the guide wire lumen, wherein the portion of the shaft between the rapid exchange port and the proximal portion of the shaft is solid.

9. The catheter apparatus of any of examples 1-8 wherein:
between the rapid exchange port and the distal portion of the shaft, the shaft has a first outer diameter; and
between the rapid exchange port and the proximal portion of the shaft, the shaft has a second outer diameter less than the first outer diameter.

10. The catheter apparatus of any of examples 1-9 wherein the elongated shaft further comprises monofilaments interspersed with the wires of the first and second thermocouple assemblies.

11. The catheter apparatus of any of examples 1-10 wherein the first and/or second thermocouple assemblies have a first pitch at the proximal portion of the shaft and a second pitch at the distal portion of the shaft, wherein the first pitch is less than the second pitch.

12. The catheter apparatus of any of examples 1-11 wherein shaft further includes a braiding element wrapped around the shaft.

13. The catheter apparatus of example 12 wherein the braiding element is intertwined with the first and/or second thermocouple assemblies.

14. A neuromodulation catheter, comprising:
an elongate polymer shaft comprising multiple thermocouple wires arranged thereabout; and
a plurality of neuromodulation elements operably coupled to the polymer shaft at a distal portion of the polymer shaft, wherein individual neuromodulation elements are electrically coupled to corresponding pairs of thermocouple wires,
wherein—
each thermocouple wire is distributed along a helical path extending around a longitudinal axis of the polymer shaft, and wherein the thermocouple wires extending along the polymer shaft are arranged generally parallel with each other, and
at least a portion of the polymer shaft comprises a lumen therethrough sized and shaped to slidably receive a medical guide wire.

15. The neuromodulation catheter of example 14 wherein the polymer shaft comprises four pairs of thermocouple wires arranged thereabout, and wherein the plurality of neuromodulation elements comprises four gold electrodes electrically coupled to corresponding pairs of thermocouple wires.

16. The neuromodulation catheter of example 14 or example 15 wherein the polymer shaft comprises a first region and a second region along the shaft, and wherein the helical path comprises a first pitch throughout the first region, and a second pitch different than the first pitch throughout the second region.

17. The neuromodulation catheter of any of examples 14-16 wherein the distal portion of the polymer shaft is transformable between a low-profile delivery state and an expanded deployed state having a generally helical/spiral configuration.

18. A method of manufacturing a medical device, the method comprising:
positioning a first thermocouple assembly and a second thermocouple assembly about a central mandrel, wherein the first thermocouple assembly comprises a first pair of wires and the second thermocouple assembly comprises a second pair of wires;
braiding the first wires of the first thermocouple assembly and the second wires of the second thermocouple assembly along the mandrel, wherein the first wires and the second wires are spaced apart from each other and arranged in a spiral pattern along the mandrel;
disposing a polymer material over the braided first wires and second wires to form an elongated tubular shaft about the mandrel;
selectively removing portions of the polymer material at a distal region of the elongated shaft to access the first wires of the first thermocouple assembly and the second wires of the second thermocouple assembly;
electrically coupling a first electrode to the exposed portion of the first wires of the first thermocouple assembly;
electrically coupling a second electrode to the exposed portion of the second wires of the second thermocouple assembly; and
removing the mandrel from at least the distal region of the elongated shaft.

19. The method of example 18, further comprising positioning the distal region of the elongated shaft about a mandrel in a spiral configuration after removing the mandrel from at least the distal region, and wherein the method further comprises heat setting the distal region into the spiral shape.

20. The method of example 18 or example 19 wherein:
electrically coupling a first electrode to the exposed portion of the first wires comprises laser welding the first electrode to the individual first wires; and
electrically coupling a second electrode to the exposed portion of the second wires comprises laser welding the second electrode to the individual second wires.

21. The method of any of examples 18-20 wherein the distal region of the elongated shaft comprises a guide wire lumen therethrough, and wherein the method further comprises forming a rapid exchange access port along the elongated shaft and in communication with the guide wire lumen, wherein the rapid exchange access port and the guide wire lumen are sized and shaped to slidably receive a medical guide wire.

22. The method of any of examples 18-21 wherein removing the mandrel from at least the distal region of the elongated shaft comprises removing the mandrel from only the portion of the shaft distal of the rapid exchange access port such the portion of the shaft proximal of the rapid exchange access port is solid therethrough.

VI. Conclusion

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while steps may be presented in a given order, alternative embodiments may perform steps in a different order. The various embodiments described herein and elements thereof may also be combined to provide further embodiments. In some cases, well-known structures and functions have not been shown or described in detail to avoid unnecessarily obscuring the description of embodiments of the present technology.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A catheter comprising:
   a neuromodulation element; and
   an elongated shaft configured to expand from a delivery configuration to a deployed configuration, the elongated shaft comprising:
      a plurality of electrical conductors, at least one electrical conductor of the plurality of electrical conductors being electrically coupled to the neuromodulation element; and
      at least one braiding element which is at least one of intertwined or braided with the plurality of electrical conductors along a length of the elongated shaft, wherein the at least one braiding element is configured to impart the deployed configuration having a spiral shape or a helical shape upon the elongated shaft, and wherein the at least one braiding element comprises a shape-memory material.

2. The catheter of claim 1, wherein the elongated shaft comprises a plurality of braiding elements, and wherein at least two braiding elements of the plurality of braiding elements have different cross-sectional areas.

3. The catheter of claim 1, wherein the plurality of electrical conductors are braided with the at least one braiding element.

4. The catheter of claim 1, wherein the at least one braiding element comprises a polymer.

5. The catheter of claim 1,
   wherein the elongated shaft extends along a longitudinal axis,
   wherein the plurality of electrical conductors are wound about the longitudinal axis in a first direction, and
   wherein the at least one braiding element is about the longitudinal axis in a second direction, the second direction being the same as the first direction.

6. The catheter of claim 1,
   wherein the elongated shaft extends along a longitudinal axis,
   wherein the plurality of electrical conductors are wound about the longitudinal axis in a first direction, and
   wherein the at least one braiding element is wound about the longitudinal axis in a second direction, the second direction being the opposite of the first direction.

7. The catheter of claim 1, wherein the at least one braiding element does not cross over any electrical conductors of the plurality of electrical conductors.

8. The catheter of claim 1, wherein the at least one braiding element comprises a same pitch along the elongated shaft.

9. The catheter of claim 1, wherein the at least one braiding element comprises a variable pitch along the elongated shaft.

10. The catheter of claim 1, further comprising a plurality of thermocouple assemblies, each thermocouple assembly of the plurality of thermocouple assemblies comprising at least two electrical conductors of the plurality of electrical conductors.

11. The catheter of claim 10, wherein the at least two electrical conductors comprise at least two electrically conductive wires, each wire of the at least two electrically conductive wires comprises a different metal.

12. The catheter of claim 11, wherein one wire of the at least two electrically conductive wires comprises constantan and another wire of the at least two electrically conductive wires comprises copper.

13. The catheter of claim 10, wherein the neuromodulation element comprises a plurality of electrodes, wherein each electrode of the plurality of electrodes is electrically connected to a corresponding thermocouple assembly of the plurality of thermocouple assemblies.

14. A neuromodulation catheter comprising:
   a plurality of neuromodulation elements; and
   an elongated shaft configured to expand from a delivery configuration to a deployed configuration, the elongated shaft comprising:
      a plurality of thermocouple assemblies, each thermocouple assembly of the plurality of thermocouple assemblies configured to be electrically connected to a corresponding neuromodulation element of the plurality of neuromodulation elements, wherein each thermocouple assembly of the plurality of thermocouple assemblies comprises at least two electrical conductors; and at least one braiding element which is at least one of intertwined or braided with the plurality of thermocouple assemblies along a length of the elongated shaft, wherein the at least one braiding element is configured to impart the deployed configuration having a spiral shape or a helical shape upon the elongated shaft, and wherein the at least one braiding element comprises a shape-memory material.

15. The catheter of claim 14, wherein the at least one braiding element comprises a plurality of braiding elements, and wherein at least two braiding elements of the plurality of braiding elements have different cross-sectional areas.

16. The catheter of claim 14, wherein the plurality of electrode conductors are braided with the at least one braiding element.

17. The catheter of claim 14,
wherein the elongated shaft extends along a longitudinal axis,
wherein the plurality of electrical conductors are wound about the longitudinal axis in a first direction, and
wherein the at least one braiding element is wound about the longitudinal axis in a second direction, the second direction being the same as the first direction.

18. The catheter of claim 14,
wherein the elongated shaft extends along a longitudinal axis,
wherein the plurality of electrical conductors are wound about the longitudinal axis in a first direction, and
wherein the at least one braiding element is wound about the longitudinal axis in a second direction, the second direction being the opposite of the first direction.

19. The catheter of claim 14, wherein the at least one braiding element does not cross over any electrical conductors of the plurality of electrical conductors.

20. The catheter of claim 14, wherein for each thermocouple assembly of the plurality of thermocouple assemblies, the at least two electrical conductors comprises two electrically conductive wires, each wire of the at least two electrically conductive wires comprising a different metal.

* * * * *